United States Patent [19]

Koros et al.

[11] Patent Number: 5,262,056
[45] Date of Patent: Nov. 16, 1993

[54] POLYAMIDES AND POLYPYRROLONES FOR FLUID SEPARATION MEMBRANES

[75] Inventors: William J. Koros; David R. B. Walker, both of Austin, Tex.

[73] Assignee: Board of Regents, The University of Texas System, Austin, Tex.

[21] Appl. No.: 986,053

[22] Filed: Nov. 30, 1992

[51] Int. Cl.$^5$ .............................................. B01D 71/32
[52] U.S. Cl. ............................. 210/654; 210/500.33; 210/500.39
[58] Field of Search .................... 55/16, 158; 528/125; 210/634, 644, 649–654, 500.21, 500.27, 500.31, 500.33, 500.37–500.39

[56] References Cited

U.S. PATENT DOCUMENTS

| | | | |
|---|---|---|---|
| 2,894,988 | 7/1959 | Cryer | 260/581 |
| 3,518,232 | 6/1970 | Bell | 260/78 |
| 3,657,190 | 4/1972 | Hughes et al. | 260/65 |
| 3,792,024 | 2/1974 | Saferstein | 260/78 |
| 4,705,540 | 11/1987 | Hayes | 55/16 |
| 4,717,394 | 1/1988 | Hayes | 55/16 |
| 4,944,880 | 7/1990 | Ho et al. | 210/640 |
| 4,946,594 | 8/1990 | Thaler et al. | 210/651 |
| 4,990,275 | 2/1991 | Ho et al. | 252/62.3 |
| 4,997,906 | 3/1991 | Thaler et al. | 528/272 |
| 5,074,891 | 12/1991 | Kohn et al. | 55/16 |

FOREIGN PATENT DOCUMENTS

0446947A2  9/1991  European Pat. Off. .

OTHER PUBLICATIONS

Bell and Jewell, "Synthesis and Properties of Polyimidazopyrrolones," *Journal of Polymer Science*, Part A-1, 5:3013–3060, 1967, published in U.S.A.
Bell and Pezdirtz, "Polyimidazopyrrolones: A New route to Ladder Polymers," *Polymer Letters*, 3:977–984, 1965, published in U.S.A.
Berlin et al.,. "Thermostable Polymers from Dianhydrides of Aromatic Tetracarboxylic Acids and Tetra-Amines," *Russian Chemical Reviews*, 40(3):284–300, 1971, published in Russia.
Berry and Eisaman, "Cryoscopy on Sulfuric Acid Solutions of a Heterocyclic Polymer (BBB) and Related Compounds," *Journal of Polymer Science*, 12:2253–2266, 1974, published in U.S.A.
Bruma and Marvel, "Synthesis of a Pyrrolone-Type Polymer Containing Anthraquinone Units in Molten Antimony Trichloride," *Journal of Polymer Science*, 12:2385–2389, 1974, published in U.S.A.
Colson et al., "Polybenzoylenebenzimidazoles," *Journal of Polymer Science*, 4:59–70, 1966, published in U.S.A.
Dawans and Marvel, "Polymers from ortho Aromatic Tetraamines and Aromatic Dianhydrides," *Journal of Polymer Science*, 3:3549–3571, 1965, published in U.S.A.
Koros and Walker, "Gas Separation Membrane Material Selection Criteria: Weakly and Strongly Interacting Feed Component Situations," *Polymer Journal*, 23(5):481–490, 1991, published in Japan.
Scott et al., "Polyimidazopyrrolone Reverse Osmosis Membranes," *Polymer Letters*, 8:563–571, 1970, published in U.S.A.

(List continued on next page.)

*Primary Examiner*—Frank Sever
*Attorney, Agent, or Firm*—Arnold, White & Durkee

[57] ABSTRACT

Polyamide and polypyrrolone membranes for fluid separation having desirable permeabilities, solubilities, diffusivities,, high glass transition temperatures and large fractional free volumes. In particular, the membranes are the polyamide and polypyrrolone forms of hexafluoroisopropylidene-bisphthalic anhydride polymerized with 3,3',4,4' tetraaminodiphenylisopropylidene (6FDA-TADPIP) and polymerized with hexafluorotetraamine (6FDA-6FTA). Fluid separation membranes made from these polymers are described as well as a method of separating fluids using these membranes. Pure gas permeabilities and permeabilities with gas feed mixtures using the fluid separation membranes for feed pressures up to 900 psia indicate desirable permeability and no plasticization effects.

2 Claims, 12 Drawing Sheets

OTHER PUBLICATIONS

Walker and Koros, "Transport Characterization of a Polypyrrolone for Gas Separations," *Journal of Membrane Science*, 55:99–117, 1991, published in Europe.

Dialog Search Report, printed in U.S.A.

Kim et al., "Relationship Between Gas Separation PRC Properties and Chemical Structure in a Series of Aromatic Polyimides," *Journal of Membrane Science*, 37:45–62, 1988, published in Europe.

Foster and Marvel, "Polybenzimidazoles. IV. Polybenzimidazoles Containing Aryl Ether Linkages," *Journal of Polymer Science*, Part A, 3:417–421, 1965, published in U.S.A.

Sulzberg and Cotter, "Synthesis and Polymerization of a Dinitrobisphenol A: A New Polycarbonate Synthesis," *Polymer Letters*, 7:185–191, 1969, published in U.S.A.

Bondi, A. A., "Catalog of Molecular Properties," in: *Physical Properties of Molecular Crystals, Liquids and Gasses*, Chapter 14, pp. 450–471, Wiley, New York, New York, publishers, 1968, published in U.S.A.

Coleman, Maria Rosario, "Isomers of Fluorine-Containing Polyimides for Gas Separation Membranes", Abstract from Ph.D. dissertation, 1992, published in U.S.A.

Kim, Tae-Han, "Gas Sorption and Permeation in a Series of Aromatic Polyimides", Abstract from Ph.D. disseration, 1988, published in U.S.A.

Kim et al., "Advanced Gas Separation Membrane Materials: Rigid Aromatic Polyimides," *Separation Science and Technology*, 23(12 & 13):1611–1626, 1988, published in U.S.A.

Van Krevelen, D. W., and Huftyzer, P. J., "Volumetric Properties," in: *Properties of Polymers, Their Estimation and Correlation with Chemical Structure*, 2nd edn., Elsevier, New York, N.Y., publishers, pp. 14–55, 1976, published in U.S.A.

A: Thermostatted Chamber
B: Permeation Cell
C: Thermostatted Chamber
D: Safety Rupture Device
E: Downstream Receiver Volume
F: Baratron Transducer
G: Vacuum Pump
H: Upstream Hiese Pressure Gage
I: Ballast Volume
J: Supply Gas Cylinder

POLYAMIDES AND POLYPYRROLONES FOR FLUID SEPARATION MEMBRANES

The present invention relates generally to fluid separation membrane polymers and more specifically to techniques utilizing a polypyrrolode polymer for fluid separation membranes.

BACKGROUND OF THE INVENTION

Permeable membranes are known to separate or selectively enrich a gas mixture. For example, membranes are used in the separation of $H_2$ from supercritical gases such as $N_2$, CO and $CH_4$; the separation of $CO_2$ and water vapor; and the enrichment of air by nitrogen or oxygen. Hydrogen is recovered from ammonia production plants using large scale membrane technology.

The permeability, P, of a gaseous penetrant can be written as the product of an effective solubility of the penetrant in the polymer matrix, S, and an average diffusivity of the penetrant through the polymer matrix, D.

$$P = D\,S \tag{1}$$

The average penetrant diffusivity, D, can be determined by dividing the penetrant's permeability by the penetrant's solubility coefficient. With negligible downstream pressure, the solubility coefficient, S, is equal to the secant slope of the gas sorption isotherm evaluated at the upstream conditions. The solubility coefficient is thermodynamic in nature, and is affected by the inherent condensability of the penetrant, polymer-penetrant interactions, and the amount of excess or free volume existing in the glassy polymer. Increases in either D or S will tend to increase the permeability coefficient; however, permselectivity must also be considered in structural modifications to avoid undesirable trade-offs between productivity and selectivity.

Since the downstream pressure is nearly zero, the gas separation factor for a mixture of gases A and B, $\alpha_{A/B}$, defined by eqn. (2) is rigorously equal to the ideal separation factor based on the individual permeabilities of the two gases A and B, $\alpha^*_{A/B}$, given by eqn. (3):

$$\alpha_{A/B} = \frac{[y_A/y_B]}{[x_A/x_B]} \tag{2}$$

$$\alpha_{A/B}^* = \frac{P_A}{P_B} \tag{3}$$

where $x_i$'s and $y_i$'s are the mole fractions of components A and B at the upstream and downstream sides of the membrane, respectively. The ideal separation factor, $\alpha^*_{A/B}$, provides a measure of the intrinsic permselectivity of a membrane material for mixtures of A and B. In the absence of plasticizing effects due to strong polymer-penetrant interactions, $\alpha^*_{A/B}$ in mixed gas situations can be approximated to within about 10% using the more easily measured ratio of permeabilities of pure gases A and B.

If eqn. (1) is substituted into eqn. (3), the ideal separation factor can be separated into two parts:

$$\alpha_{A/B}^* = \left[\frac{D_A}{D_B}\right]\left[\frac{S_A}{S_B}\right] \tag{4}$$

where $D_A/D_B$ is the diffusivity selectivity, and $S_A/S_B$ is the solubility selectivity. The diffusivity selectivity is determined by the ability of the polymer to discriminate between the penetrants on the basis of their sizes and shapes, and is governed by intrasegmental motions and intersegmental packing. The importance of steric factors is demonstrated by the greater diffusivity of carbon dioxide over methane despite the fact that methane has the lower molecular weight of the two molecules. The solubility selectivity, like the solubility, is thermodynamic in nature. Experience has shown that this factor is difficult to adjust without causing significant losses in the diffusivity selectivity. The key to structure-property optimization for gas separation membranes, then, is finding means to increase the diffusivity selectivity without incurring large reductions in the diffusivity of the desired component, A.

Significant increases in diffusivity and diffusivity selectivity can be obtained by simultaneously inhibiting intrasegmental motions and intersegmental chain packing. These results can be simmarized as two principles for tailoring membrane materials:

1. structural moieties which inhibit chain packing while simultaneously inhibiting torsional motion about flexible linkages on the polymer backbone tend to increase permeability while maintaining permselectivity;
2. structural moieties which decrease the concentration of mobile linkages in the polymer backbone and do not significantly change intersegmental packing tend to increase permselectivity without decreasing permeability significantly.

The ratio of specific free volume to polymer specific volume, the fractional free volume, is representative of the degree of openness of the matrix. This index takes into account the filling of space by bulky side groups, but is not experimentally determined. An estimate of the occupied volume of the polymer is made by using a group contribution method such as that of Bondi (1968) or Van Krevelen and Hoftyzer (1976).

Much of the work in the field has been directed to developing membranes which optimize the separation factor and total flux of a given system. It is disclosed in U.S. Pat. No. 4,717,394 to Hayes that aromatic polyimides containing the residue of alkylated aromatic diamines are useful in separating a variety of gases. Moreover, it has been reported in the literature that other polyimides, polycarbonates, polyurethanes, polysulfones and polyphenyleneoxides are useful for like purposes.

U.S. Pat. No. 5,074,891 to Kohn et al. discloses certain polyimides with the residuum of a diaryl fluorine-containing diamine moiety as useful in separation processes involving, for example, $H_2$, $N_2$, $CH_4$, CO, $CO_2$, He and $O_2$.

By utilizing a more rigid repeat unit than a polyimide, however, even greater permeability and permselectivity are realized. Such a rigid repeat unit is a polypyrrolone.

Polypyrrolones are condensation polymers obtained from the reaction of aromatic dianhydrides and aromatic tetraamines followed by complete cyclization. The polymer obtained by the initial reaction of the monomers in an aprotic solvent is a soluble poly(amide amino acid), which can be thermally cyclized. The polypyrrolone resulting from cyclization possesses a repeat unit with two benzene rings joined by two fused five membered rings, imparting a great degree of thermal and chemical resistance, strength and rigidity. The rigidity of the polypyrrolone repeat unit provides unusually high size and shape discrimination between the penetrants. With the incorporation of the proper linkages in the repeat unit, the intrinsic rigidity of the polypyrrolone linkage can also inhibit packing, allowing one to increase penetrant mobility without losses in selectivity.

Polypyrrolones as membrane materials were proposed and studied originally for the reverse osmosis purification of water by H. Scott et al. (1970).

The syntheses, permeabilities, solubilities and diffusivities of the polyimides, 6FDA-6F$_p$DA, 6FDA-IPDA, 6FDA-ODA, 6FDA-DAF and the polypyrrolone 6FDA-TADPO have been described (Walker and Koros, 1991; Koros and Walker, 1991; Kim et al. 1988a, b; Kim 1988c; Coleman, 1992). Their structures, permeabilities, solubilities, diffusivities, glass transition temperatures and fractional free volumes are shown in Tables 1–10.

TABLE 1

Pure Gas Permeabilities and Ideal Permselectivities for Polyimides. Permeabilities are in units of $10^{-10}$ (cc(STP) cm/cm$^2$ sec cmHg) = 1 Barrer

| Polymer | $P_{He}$ | $P_{O_2}$ | $P_{CO_2}$ | $\frac{He}{CH_4}$ | $\frac{O_2}{N_2}$ | $\frac{CO_2}{CH_4}$ |
|---|---|---|---|---|---|---|
| 6FDA-ODA | 51.5 | 4.34 | 23.0 | 135.4 | 5.2 | 60.5 |
| 6-FDA-IPDA | 71.2 | 7.53 | 30.0 | 102.1 | 5.6 | 42.9 |
| 6FDA-DAF | 98.5 | 7.85 | 32.2 | 156.3 | 6.2 | 51.1 |
| 6FDA-6FpDA | 137 | 16.3 | 63.9 | 85.6 | 4.7 | 39.9 |

TABLE 2

Pure Gas Permeabilities and Ideal Permselectivities for the 6FDA-TADPO Polyamide. Permeabilities are in units of $10^{-10}$ (cc(STP) cm/cm$^2$ sec cmHg) = 1 Barrer

| Polymer | $P_{He}$ | $P_{O_2}$ | $P_{CO_2}$ | $\frac{He}{CH_4}$ | $\frac{O_2}{N_2}$ | $\frac{CO_2}{CH_4}$ |
|---|---|---|---|---|---|---|
| 6FDA-TADPO | 19.1 | 0.97 | 3.69 | 230.9 | 5.8 | 44.5 |

TABLE 3

Pure Gas Permeabilities and Ideal Permselectivities for the 6FDA-TADPO Polypyrrolone.
Permeabilities are in units of $10^{-10}$ (cc(STP) cm/cm$^2$ sec cmHg) = 1 Barrer

| Polymer | $P_{He}$ | $P_{O_2}$ | $P_{CO_2}$ | He/CH$_4$ | O$_2$/N$_2$ | CO$_2$/CH$_4$ |
|---|---|---|---|---|---|---|
| 6FDA-TADPO | 90.2 | 7.9 | 27.4 | 171.5 | 6.5 | 52.2 |

TABLE 4

Pure Gas Solubilities and Solubility Selectivities for Polyimides.
Solubilities are in units of (cc(STP)/cc atm).

| Polymer | $S_{He}$ | $S_{O_2}$ | $S_{CO_2}$ | He/CH$_4$ | O$_2$/N$_2$ | CO$_2$/CH$_4$ |
|---|---|---|---|---|---|---|
| 6FDA-ODA | 0.079 | 1.03 | 4.89 | 0.060 | 1.90 | 3.70 |
| 6FDA-IPDA | 0.079 | 0.9 | 4.24 | 0.066 | 1.81 | 3.53 |
| 6FDA-DAF | 0.096 | 1.20 | 5.02 | 0.060 | 1.78 | 3.14 |
| 6FDA-6FpDA | 0.072 | 0.99 | 5.99 | 0.051 | 1.48 | 4.16 |

TABLE 5

Pure Gas Solubilities and Solubility Selectivities for the 6FDA-TADPO Polyamide.
Solubilities are in units of (cc(STP)/cc atm).

| Polymer | $S_{He}$ | $S_{O_2}$ | $S_{CO_2}$ | He/CH$_4$ | O$_2$/N$_2$ | CO$_2$/CH$_4$ |
|---|---|---|---|---|---|---|
| 6FDA-TADPO | 0.067 | 0.55 | 3.06 | 0.085 | 1.46 | 3.87 |

TABLE 5-continued

Pure Gas Solubilities and Solubility Selectivities for the 6FDA-TADPO Polyamide.
Solubilities are in units of (cc(STP)/cc atm).

| Polymer | $S_{He}$ | $S_{O_2}$ | $S_{CO_2}$ | $\dfrac{He}{CH_4}$ | $\dfrac{O_2}{N_2}$ | $\dfrac{CO_2}{CH_4}$ |
|---|---|---|---|---|---|---|

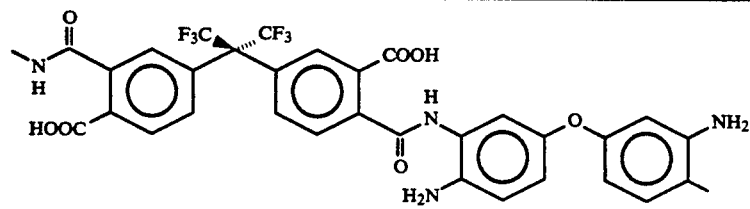

TABLE 6

Pure Gas Solubilities and Solubility Selectivities for the 6FDA-TADPO Polypyrrolone.
Solubilities are in units of (cc(STP)/cc atm).

| Polymer | $S_{He}$ | $S_{O_2}$ | $S_{CO_2}$ | $\dfrac{He}{CH_4}$ | $\dfrac{O_2}{N_2}$ | $\dfrac{CO_2}{CH_4}$ |
|---|---|---|---|---|---|---|
| 6FDA-TADPO | 0.103 | 1.09 | 4.65 | 0.060 | 1.161 | 2.71 |

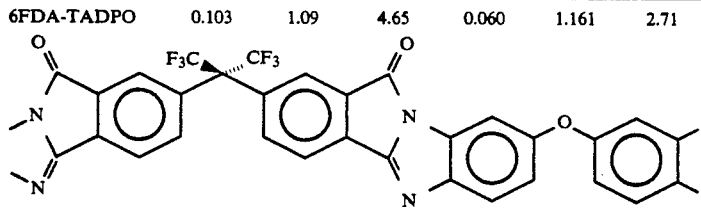

TABLE 7

Pure Gas Diffusivities and Diffusivity Selectivities for Polyimides.
Diffusivities are in units of $10^{-10}$ cm$^2$/sec.

| Polymer | $D_{He}$ | $D_{O_2}$ | $D_{CO_2}$ | $\dfrac{He}{CH_4}$ | $\dfrac{O_2}{N_2}$ | $\dfrac{CO_2}{CH_4}$ |
|---|---|---|---|---|---|---|
| 6FDA-ODA | 49500 | 320 | 358 | 2262 | 2.75 | 16.3 |
| 6FDA-IPDA | 68500 | 636 | 538 | 1546 | 3.14 | 12.1 |
| 6FDA-DAF | 78000 | 497 | 488 | 2608 | 3.47 | 16.3 |
| 6FDA-6FpDA | 145000 | 1250 | 811 | 1678 | 3.18 | 9.6 |

TABLE 7-continued

Pure Gas Diffusivities and Diffusivity Selectivities for Polyimides.
Diffusivities are in units of $10^{-10}$ cm$^2$/sec.

| Polymer | $D_{He}$ | $D_{O_2}$ | $D_{CO_2}$ | $\frac{He}{CH_4}$ | $\frac{O_2}{N_2}$ | $\frac{CO_2}{CH_4}$ |
|---|---|---|---|---|---|---|

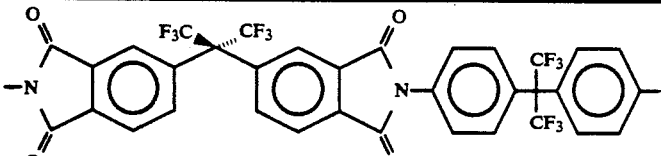

TABLE 8

Pure Gas Diffusivities and Diffusivity Selectivities for the 6FDA-TADPO Polyamide.
Diffusivities are in units of $10^{-10}$ cm$^2$/sec.

| Polymer | $D_{He}$ | $D_{O_2}$ | $D_{CO_2}$ | $\frac{He}{CH_4}$ | $\frac{O_2}{N_2}$ | $\frac{CO_2}{CH_4}$ |
|---|---|---|---|---|---|---|
| 6FDA-TADPO | 21600 | 135 | 92 | 2708 | 4.01 | 11.5 |

TABLE 9

Pure Gas Diffusivities and Diffusivity Selectivities for the 6FDA-TADPO Polypyrrolone.
Diffusitivities are in units of $10^{-10}$ cm$^2$/sec.

| Polymer | $D_{He}$ | $D_{O_2}$ | $D_{CO_2}$ | $\frac{He}{CH_4}$ | $\frac{O_2}{N_2}$ | $\frac{CO_2}{CH_4}$ |
|---|---|---|---|---|---|---|
| 6-FDA-TADPO | 66500 | 549 | 448 | 2858 | 5.9 | 19.3 |

TABLE 10

Glass Transition Temperatures and Fractional Free Volumes for Polyimides, Polyamides and Polypyrrolones

| Polymer | Glass Transition Tg, °C. | Fractional Free Volme |
|---|---|---|
| *Properties of the Polyimides.* | | |
| 6FDA-ODA | 304 | 0.1635 |
| 6FDA-IPDA | 310 | 0.1680 |
| 6FDA-DAF | 394 | 0.1588 |
| 6FDA-6FpDA | 320 | 0.1897 |
| *Properties of the Polyamides* | | |
| 6FDA-TADPO | Ring Closure | 0.1476 |
| *Properties of the Polypyrrolones.* | | |
| 6FDA-TADPO | ~375 | 0.1956 |

The 6FDA-TADPO polypyrrolone shows attractive transport properties, high permeabilities and good selectivities for all gas pairs studied. The 6FDA-TADPO polypyrrolone is structurally similar to -the 6FDA-ODA polyamide. Both polymers have an ether linkage and a hexafluoroisopropylidene linkage as part of their repeat units. As shown in Tables 1 and 3 of pure gas measurements, the 6FDA-TADPO polypyrrolone is more permeable than the 6FDA-ODA polyimide and is more selective with the exception of the carbon dioxide/methane gas pair.

The 6FDA-TADPO polypyrrolone has the highest diffusivity selectivity for all pure gas pairs, the highest glass transition temperature and the greatest free fractional volume. In the case of mixed gas permeation of carbon dioxide and methane, the 6FDA-TADPO is more selective (FIG. 10).

Once the densities of polymers are known, the specific free volumes and specific volumes can be used to estimate the fractional free volume. The fractional free volume is the ratio of the specific free volume to the specific volume of the polymer. The specific free volume is estimated by a group contribution method and the specific volume is determined by dividing the molecular weight of the repeat unit by the bulk polymer density.

The fractional free volume gives a measure of the degree of openness of the polymeric matrix. Materials with larger fractional free volumes have greater diffusivities and thus greater permeabilities than materials with smaller fractional free volumes. The polypyrrolones have fractional free volumes that are greater than the polyimides, so the diffusivities are greater than the polyimides.

The fractional free volume does not give any indication as to the selectivity of a polymer. Within a given polymer family however, polymers with greater fractional free volumes may have lower diffusivity selectivities and thus lower permselectivities. The repeat unit of a polypyrrolone is more rigid than a structurally- similar polyimide, as given by the geometry of the fused ring system and the higher glass transition temperature shown in table 10. Given the greater rigidity of the polypyrrolones, polypyrrolones with fractional free volumes similar to polyimides may have greater diffusivity selectivities and thus greater permselectivities.

The 6FDA-TADPO has half the carbonyl concentration per repeat unit as the 6FDA-ODA, effecting a lower solubility of carbon dioxide in the polypyrrolone. The lower solubility of carbon dioxide together with the rigid fused ring system of the polypyrrolone repeat unit resulted in a greater resistance to penetrant induced permeability increases and selectivity decreases referred to as plasticization.

Plasticization is caused by highly sorbing penetrants, such as carbon dioxide at higher pressures and leads to a significant deleterious loss in permselectivity. The presence of the highly sorbing penetrants leads to a softening of the polymer matrix, much as a liquid solvent or swelling agent would. The loss in permselectivity may also be accompanied by a simultaneous increase in permeability of one or more of the feed components.

The 6FDA-TADPO polypyrrolone and the 6FDA-DAF polyimide are structurally similar with both repeat units having a rigid, flat fused ring system. The transport properties of the polyimide and the polypyrrolone are similar.

The greater permeability of the polypyrrolone can be attributed to the greater fractional free volume of the polypyrrolone. The inherent rigidity of the fused ring system and the absence of a rotatable bond which is present in the polyimides accounts for the greater selectivity of the polypyrrolone.

The present invention provides for polyamide and polypyrrolone membranes for fluid separation with superior permeabilities, solubilities and diffusivities as compared to known materials.

| LIST OF ABBREVIATIONS | |
|---|---|
| 6FDA | Hexafluoroisopropylidene-bisphthalic anhydride. |
| 6FTA | Hexafluorotetraamine |
| ODA | 4,4'-Oxydianiline |
| DAF | 2,7-Diaminofluorene |
| 6FpDA | 4,4'-(Hexafluoroisopropylidene)-Dianiline |
| IPDA | 4,4'-(Isopropylidene)-Dianiline |
| TADPO | 3,3',4,4'-Tetraaminodiphenyl ether. |
| TABP | 3,3',4,4'-Tetraaminobiphenyl. |
| TADPIP | 3,3',4,4'-Tetraaminodiphenyl isopropylidene. |
| Polyamide | Initial form of polymer from condensation reaction of dianhydride and tetraamine. |
| Polypyrrolone | Final form of polymer after thermal curing to 285-300° C. |

SUMMARY OF THE INVENTION

Polyamide and polypyrrolone membranes for fluid separation having improved permeabilities, solubilities, diffusivities, a higher glass transition temperature and a larger fractional free volume are described. The tetraamine monomers, tetraaminodiphenylisopropylidene

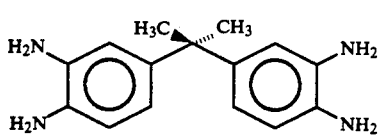

and hexafluorotetraamine

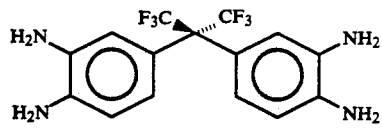

as well as the syntheses thereof are important aspects of the present invention.

A polymer having recurring units of the chemical formula

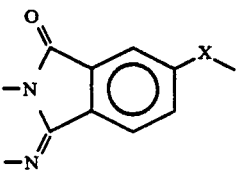

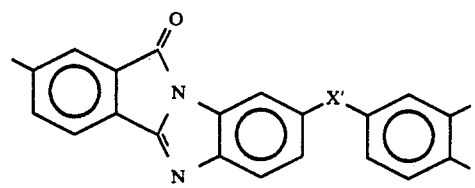

where X and X' are independently

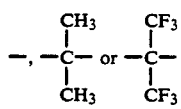

is a preferred embodiment of the invention. The number of recurring units may be from about 10 to about 2000 in this polymer. The polyamide form of this polymer is

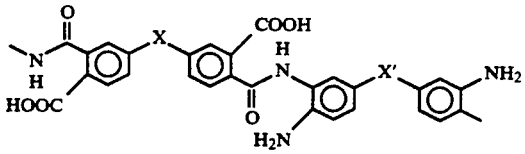

where X and X' are independently

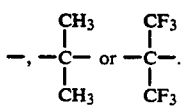

This polymer may also have from about 10 to about 2000 recurring units. Polymers having recurring units of the chemical formulas:

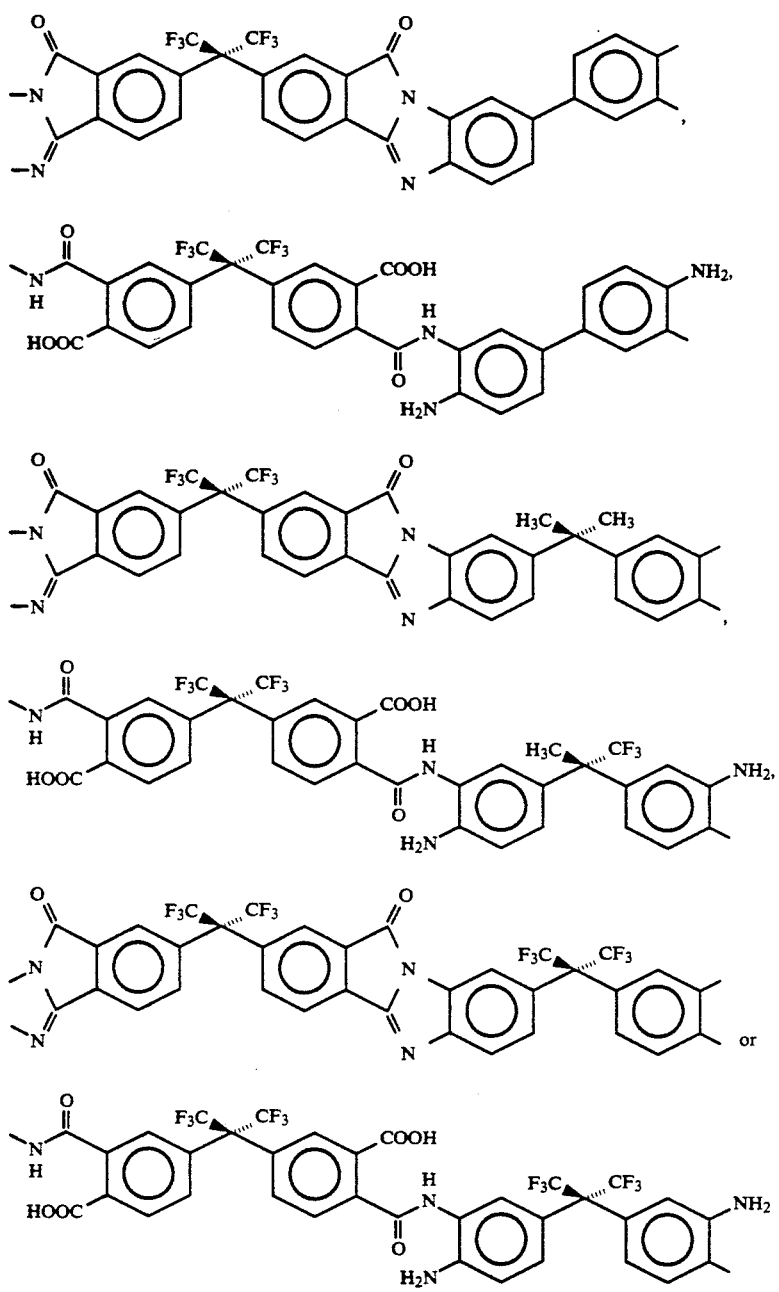

are preferred embodiments of the present invention.

Another embodiment is a polypyrrolone or polyamide membranous structure which is a polymerization product of an aromatic tetraacid or tetraacid dianhydride or bis-ortho-ester-acid halide and tetraaminodiphenylisopropylidene. Also, a polypyrrolone or polyamide membranous structure which is a polymerization product of an aromatic tetraacid or tetraacid dianhydride or bis-ortho-ester-acid halide and hexafluorotetraamine is claimed. A poly(imide-co-pyrrolone) membranous structure which is a polymerization product of an aromatic tetraacid or tetraacid dianhydride or bis-ortho-ester-acid halide and a mixture of an aromatic tetraamine and an aromatic diamine is claimed. The aromatic tetraacid or tetraacid dianhydride or bis-ortho-ester-acid halide is an ortho- or para-paired dianhydride or a bis-ortho-ester-acid chloride.

A preferred embodiment of the present invention is a fluid separation membrane comprising a polymer having recurring units of the chemical formula

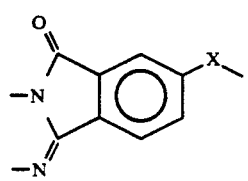

-continued

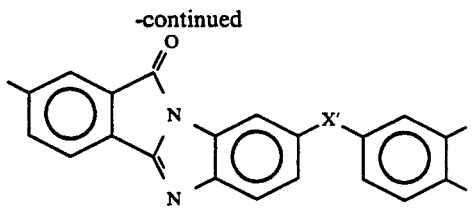

where X and X' are independently

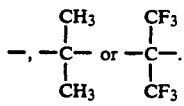

This membrane may have from about 10 to about 2000 recurring units.

Also claimed is a fluid separation membrane comprising a polymer having recurring units of the chemical formula

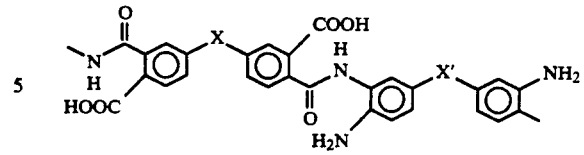

where X and X' are independently

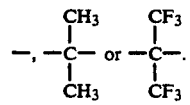

By fluids we mean gases, vapors and liquids. Preferred fluid separation is gas separation, pervaporation and vapor permeation. Again the number of recurring units in this polyamide polymer membrane may be from about 10 to about 2000. A further preferred embodiment of the present invention is a fluid separation membrane comprising a polymer having recurring units of the chemical formula

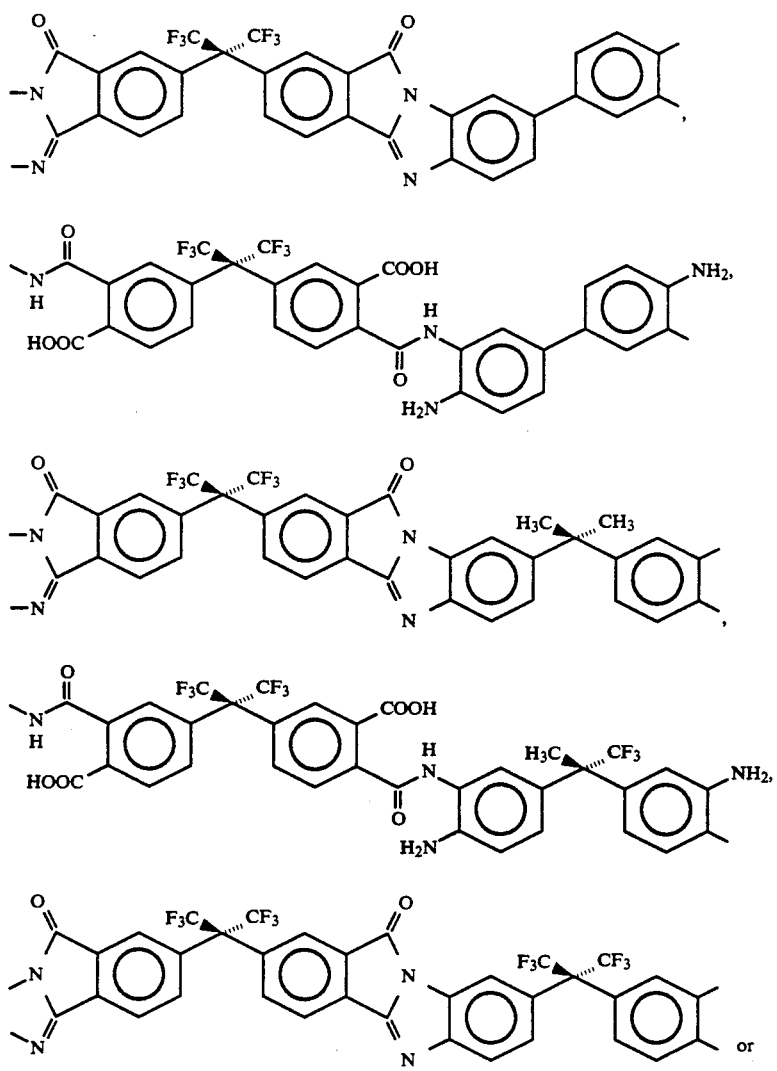

-continued

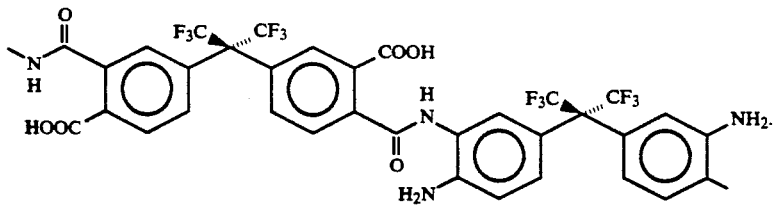

Another aspect of the present invention is a fluid separation membrane comprising a polymer which is a polymerization product of an aromatic tetraacid or tetraacid dianhydride or bis-ortho-ester-acid halide and tetraaminodiphenylisopropylidene. Also claimed is a fluid separation membrane comprising a polymer which is a polymerization product of an aromatic tetraacid or tetraacid dianhydride or bis-ortho-ester-acid halide and hexafluorotetraamine. The fluid separation membrane comprising a polymer may also be a polymerization product of an aromatic tetraacid or tetraacid dianhydride or bis-ortho-ester-acid halide and a mixture of an aromatic tetraiiine and an aromatic diamine. The aromatic tetraacid or tetraacid dianhydride or bis-ortho-ester-acid halide is an ortho- or para-paired dianhydride or a bis-ortho-ester-acid chloride.

A particularly preferred embodiment of the present invention is a method of separating two or more fluids comprising the step of bringing a mixture of two or more fluids into contact with one side of a permselective membrane comprising a polymer which is a polymerization product of an aromatic tetraanhydride having the structure

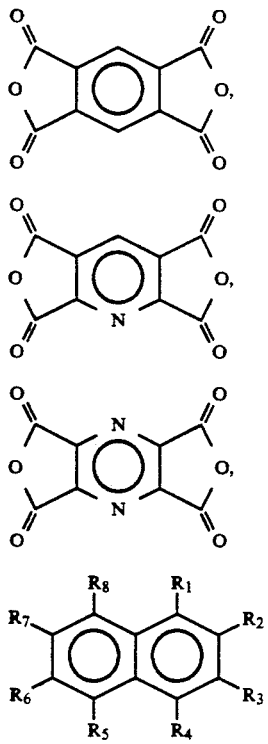

or

-continued

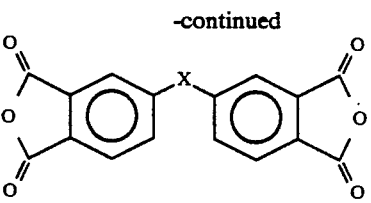

wherein at least 2 of $R_1$ and $R_2$, $R_2$ and $R_3$, $R_3$ and $R_4$, and $R_1$ and $R_4$ are carboxylic acid anhydride groups and at least two of $R_5$ and $R_6$, $R_6$ and $R_7$, $R_7$ and $R_8$, and $R_5$ and $R_8$ are carboxylic acid anhydride groups, with an aromatic tetraamine having the structure

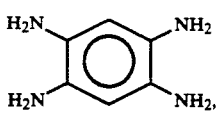

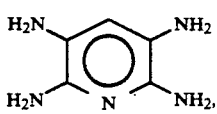

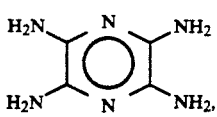

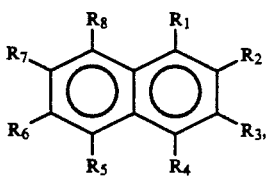

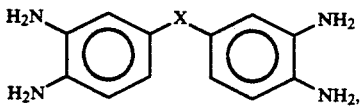

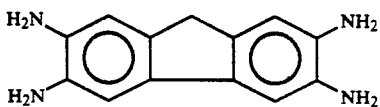

or

-continued

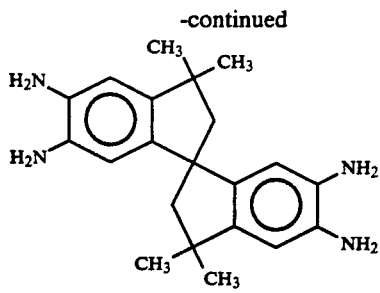

where at least 2 $R_1$ and $R_2$, $R_2$ and $R_3$, $R_3$ and $R_4$, $R_1$ and $R_8$, and $R_1$ and $R_4$ are paired amine groups and at least two of $R_5$ and $R_6$, $R_6$ and $R_7$, $R_7$ and $R_8$, $R_4$ and $R_5$, and $R_5$ and $R_8$ are paired amine groups. Preferred pairs are $R_1$ and $R_2$ with $R_5$ and $R_6$, $R_2$ and $R_3$ with $R_6$ and $R_7$, and $R_1$ and $R_8$ with $R_4$ and $R_5$.

X is:

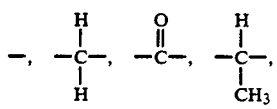

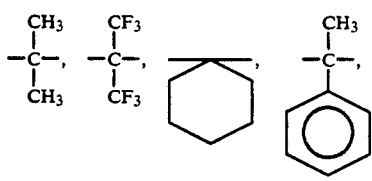

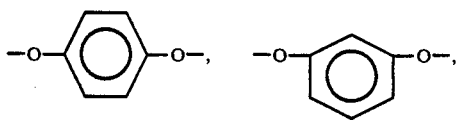

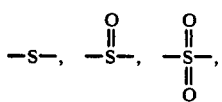

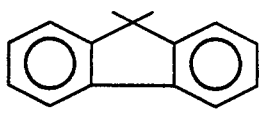

or

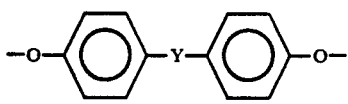

where Y is any one of the X groups preceding

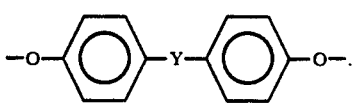

Preferred X groups are

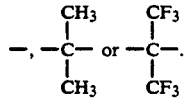

The method of separation involves one of the fluids being separated by transversing the membrane at a different rate than at least one other fluid. Transversing the membrane is passing from one side of the membrane to the other.

Another embodiment of the invention is a method of separating two or more fluids comprising the step of bringing a mixture of two or more fluids into contact with one side of a permselective membrane which is formed from an aromatic polypyrrolone having recurring units of the formula

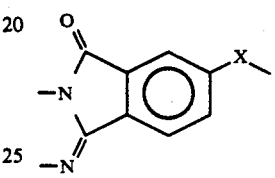

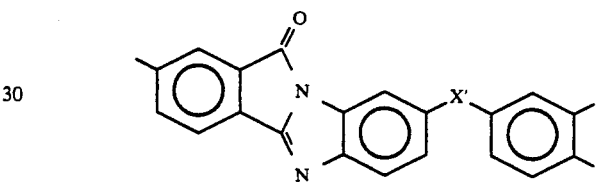

where X and X' are independently

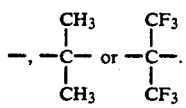

In this method, one of the fluids being separated transverses the membrane at a different rate than at least one other fluid. There may be n recurring units in the polymer of this membrane and n is preferably from about 10 to about 2000.

A further embodiment is a method of separating two or more fluids comprising the step of bringing a mixture of two or more fluids into contact with one side of a permselective membrane which is a polymerization product of an aromatic tetraacid or tetraacid dianhydride or bis-ortho-ester-acid halide and a tetraamine other than tetraaminodiphenyloxide, wherein one of the fluids being separated transverses the membrane at a different rate than at least one other fluid. The tetraacid or tetraacid dianhydride or bis-ortho-ester-acid halide may be an ortho- or para-paired dianhydride or a bis-ortho-ester-acid chloride. The tetraamine may be tetraaminodiphenyl or hexafluorotetraamine or tetraaminodiphenylisopropylidene or the tetramine may be mixed with an aromatic diamine.

A further aspect of the invention is a method of synthesis of a tetraaminodiphenylisopropylidene monomer comprising the steps of: nitrating bisphenol-A to produce 2,2-bis (3-nitro-4-hydroxyphenyl)propane; aminating the 2,2-bis (3-nitro-4-hydroxyphenyl)propane to produce 2,2-bis (3-nitro-4-aminophenyl)propane; and reducing the 2,2-bis (3-nitro-4-aminophenyl)propane to produce tetraaminodiphenylisopropylidene.

Another aspect of the invention is a method of synthesis of a hexafluorotetraamine monomer comprising the steps of: nitrating hexafluoro-bisphenol-A to produce 2,2-bis(3-nitro-4-hydroxyphenyl)-1, 1,1,3,3,3,-hexafluoropropane; aminating the 2,2-bis(3-nitro-4-hydroxyphenyl)-1,1,1,3,3,3,-hexafluoropropane to produce 2,2-bis(3-nitro-4-aminophenyl)-1,1,1,3,3,3,-hexafluoropropane; and reducing the 2,2-bis(3-nitro-4-aminophenyl)-1, 1,1,3,3,3,-hexafluoropropane to produce hexafluorotetraamine.

DETAILED DESCRIPTION OF THE PREFERRED EMBODIMENTS

Figure 1:
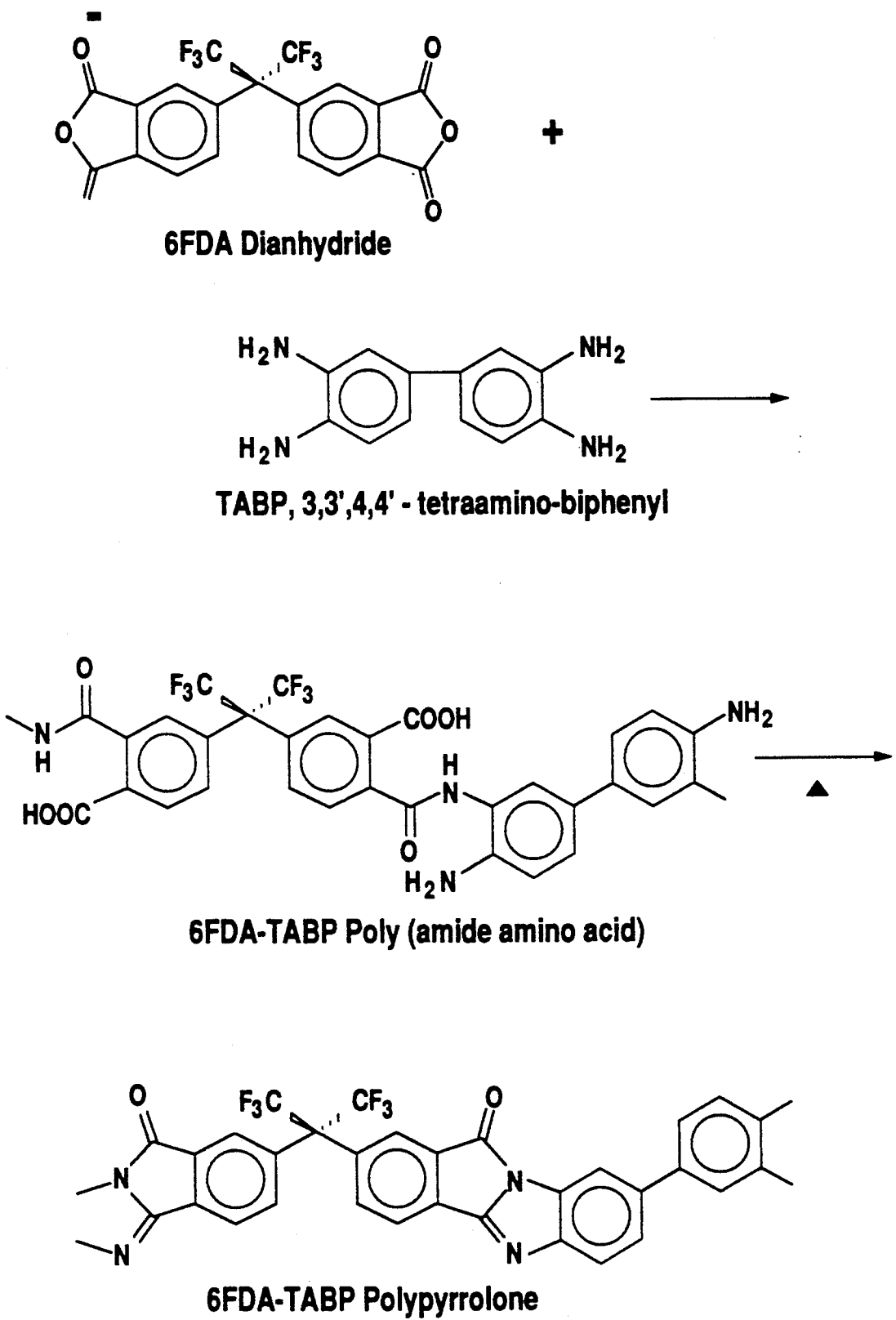
FIG. 1 shows the reaction of 6FDA dianhydride with TABP to form the polyamide amino acid of 6FDA-TABP and further thermal conversion to the 6FDA-TABP polypyrrolone.

Polypyrrolones are stepladder type polymers derived from the condensation reaction of an aromatic tetraacid derivative and an aromatic tetraamine. The resulting product is a polyamide. The remaining functional groups are reacted during a thermal curing step to form the polypyrrolone. The solvent of choice is normally an aprotic polar solvent capable of dissolving both monomers.

Aromatic Tetraacid Derivatives

The tetraacid derivative should be aromatic to produce a rigid, thermally stable, productive and selective membrane material. Tetraacids themselves lack the reactivity to produce high molecular polymer and pose the difficulty of the removal of the water formed during the reaction. One way to increase their reactivity is to utilize aromatic dianhydrides. Dianhydrides are prepared easily from the tetraacids by heating to 230° C. in a vacuum or by refluxing the tetraacid with acetic anhydride. The dianhydride can then be polymerized with the tetraamine. The acid groups should be paired into ortho pairs that are separated by at least three atoms as (1-3). The simplest compound to meet these requirements would be 1,2,4,5-benzene tetracarboxylic acid, the dianhydride of which is shown as (1). The two ortho pairs are the 1,2 pair and the 4,5 pair, and three atoms lie between the carbons of the acid groups of non-ortho pairs.

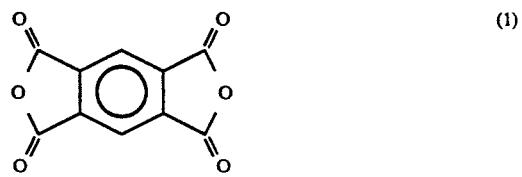

(1)

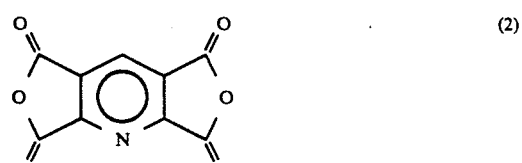

(2)

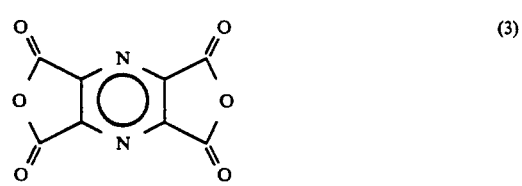

(3)

If a naphthalene (4) derivative is used, then the carboxylic acid groups may be either ortho-paired or para-paired. The most simple para-paired naphthalene type monomer would be 1,4,5,8-naphthalene tetracarboxylic acid dianhydride, of course orthopaired 1,2,5,6-naphthalene tetracarboxylic acid dianhydride or 2,3,6,7-naphthalene tetracarboxylic acid dianhydride could be used.

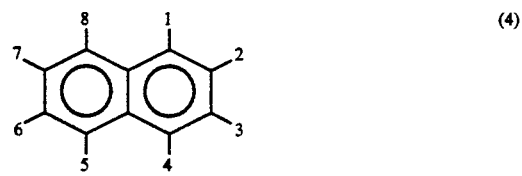

(4)

Other possible monomers would be bis-(ortho-di-acid anhydrides), which could be visualized as two phthalic acid groups joined by some connecting groups X (5).

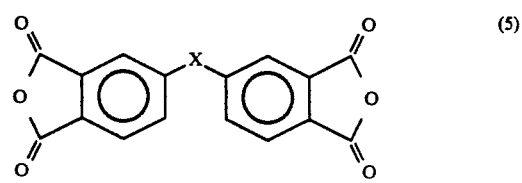

(5)

Tetraamines

The tetraamines like the tetraacid derivatives should be aromatic also for the reasons give above. The tetraamines must also be ortho-paired (6–8) or possibly para-paired if a naphthalene (9) derivative is used. Like the dianhydrides, the tetraamines may be bis-(ortho-diamines) (10), which can be visualized as two ortho-phenylene diamine molecules joined by some connector groups X(13–28). Free tetraamines or their acid salts can be used for polymerization. Since amines are easily oxidized, an inert atmosphere should be used during the polymerization.

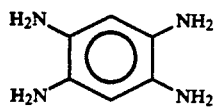 (6)

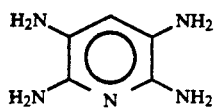 (7)

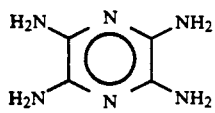 (8)

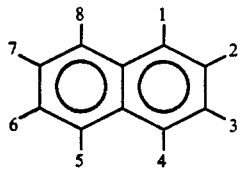 (9)

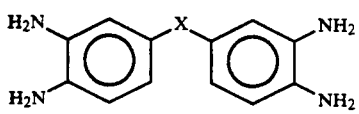 (10)

Aromatic Substrates for Totraacids and Tetraamines

Six-member rings such as benzene (1) & (6), pyridine (2) & (7), and pyrazine (3) & (8) can serve as the bases for the tetraamine and tetraacids. Fused ring systems such as naphthalene (9), fluorene (11) and tetramethyl-spiro-biindane (12) can also serve as substrates.

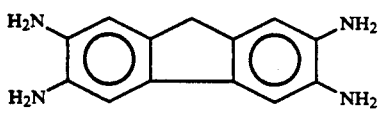 (11)

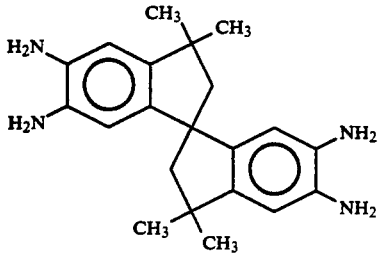 (12)

However, all four of the acid or amino groups need not be attached to the same ring, provided the four are split into ortho-pairs or para-pairs. The tetraamines can be obtained either commercially, or by the reduction of a nitro compound, or can be synthesized in three steps from a bisphenol. The method for synthesis of tetraamine from bisphenol involves the nitration of the bisphenol, the nucleophilic exchange of the hydroxyl groups for amino groups, and reduction of the amino groups. The exchange of the hydroxyl groups for amino groups is similar to the procedure described in U.S. Pat. No. 2,894,988 for the conversion of nitro-cresols to nitro-toluidines. Spirobiindane-bisphenol, which serves as a basis for useful gas separating polycarbonates, can thus be converted to a tetraamine (12) for polypyrrolone synthesis of fluid separation materials. Examples of connecting groups are shown in the list of X groups (13–28). The Y group in the last connector (28) is any one of the previous X groups (13–27).

$-$  (13)

$-O-$  (14)

$-\overset{\overset{\displaystyle H}{|}}{\underset{\underset{\displaystyle H}{|}}{C}}-$  (15)

$-\overset{\overset{\displaystyle O}{\|}}{C}-$  (16)

$-\overset{\overset{\displaystyle H}{|}}{\underset{\underset{\displaystyle CH_3}{|}}{C}}-$  (17)

$-\overset{\overset{\displaystyle CH_3}{|}}{\underset{\underset{\displaystyle CH_3}{|}}{C}}-$  (18)

$-\overset{\overset{\displaystyle CF_3}{|}}{\underset{\underset{\displaystyle CF_3}{|}}{C}}-$  (19)

cyclohexyl  (20)

$-\overset{\overset{\displaystyle CH_3}{|}}{\underset{\underset{\displaystyle C_6H_5}{|}}{C}}-$  (21)

$-O-\text{C}_6\text{H}_4-O-$  (22)

$-O-\text{C}_6\text{H}_4-O-$  (23)

$-S-$  (24)

$-\overset{\overset{\displaystyle O}{\|}}{S}-$  (25)

-continued

(26)

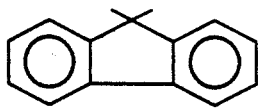
(27)

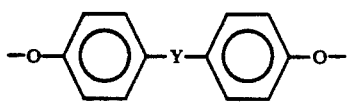
(28)

Another reactive form for the tetraacid is the bis-ortho-ester-acid chloride. This type of compound is prepared from a dianhydride by reaction with an alcohol to form a bis-(ortho-acid-ester) followed by reaction to convert acid groups to acid halides. This method prepares a very reactive monomer, but this reactivity makes the monomer more water sensitive. Additionally, larger, more slowly diffusive side product alcohol groups are given off during the final cure of the polyamide to the polypyrrolone. Tetraacid chlorides may be difficult to use due to inevitable crosslinking problems. All the acid chloride groups on one molecule could react to form a four-arm branch thus leading to a network polymer. With either the dianhydride or bis-ortho-ester-acid halide, preferably chloride, the functionality of the monomer is two, leading to linear polymer formation.

Selection of Monomers for Useful Polypyrrolone Fluid Separation Materials

At least one of the monomers should have a connecting group X (13–28) that serves as a packing inhibitor in the repeat unit of the polymer. Groups that serve as packing inhibitors include isopropylidene (18), hexafluoroisopropylidene (19), phenylethylidene (21), and fluorenylidene (27). Connector (28) would also be useful if the Y group is one of the above four groups: (18), (19), (21), or (27). The packing inhibitor could be part of the tetraacid, the tetraamine, or both. Additionally, the spriobiindane tetraamine (12) would serve as a packing inhibitor and would therefore be useful as a monomer with any dianhydride.

EXAMPLE 1

The Synthesis of Tadpip Monomer

TADPIP, 3,3', 4,4' Tetraamino-diphenyl isopropylidene, and IPDA, 4,4'-(Isopropylidene)-dianiline, are structurally similar. TADPIP was synthesized by a three step procedure starting with bisphenol-A. This method was chosen since IPDA was not available and would have to have been synthesized. The synthesis of IPDA from aniline and acetone is a low yield reaction (~50%) which requires long times (nearly a week) with many by-products. Even after the IPDA was purified, four steps of synthesis would be required to obtain TADPIP. By starting with bisphenol-A, polymer grade TADPIP was obtained with the isolation and purification of two, rather than four intermediates.

Figure 2:
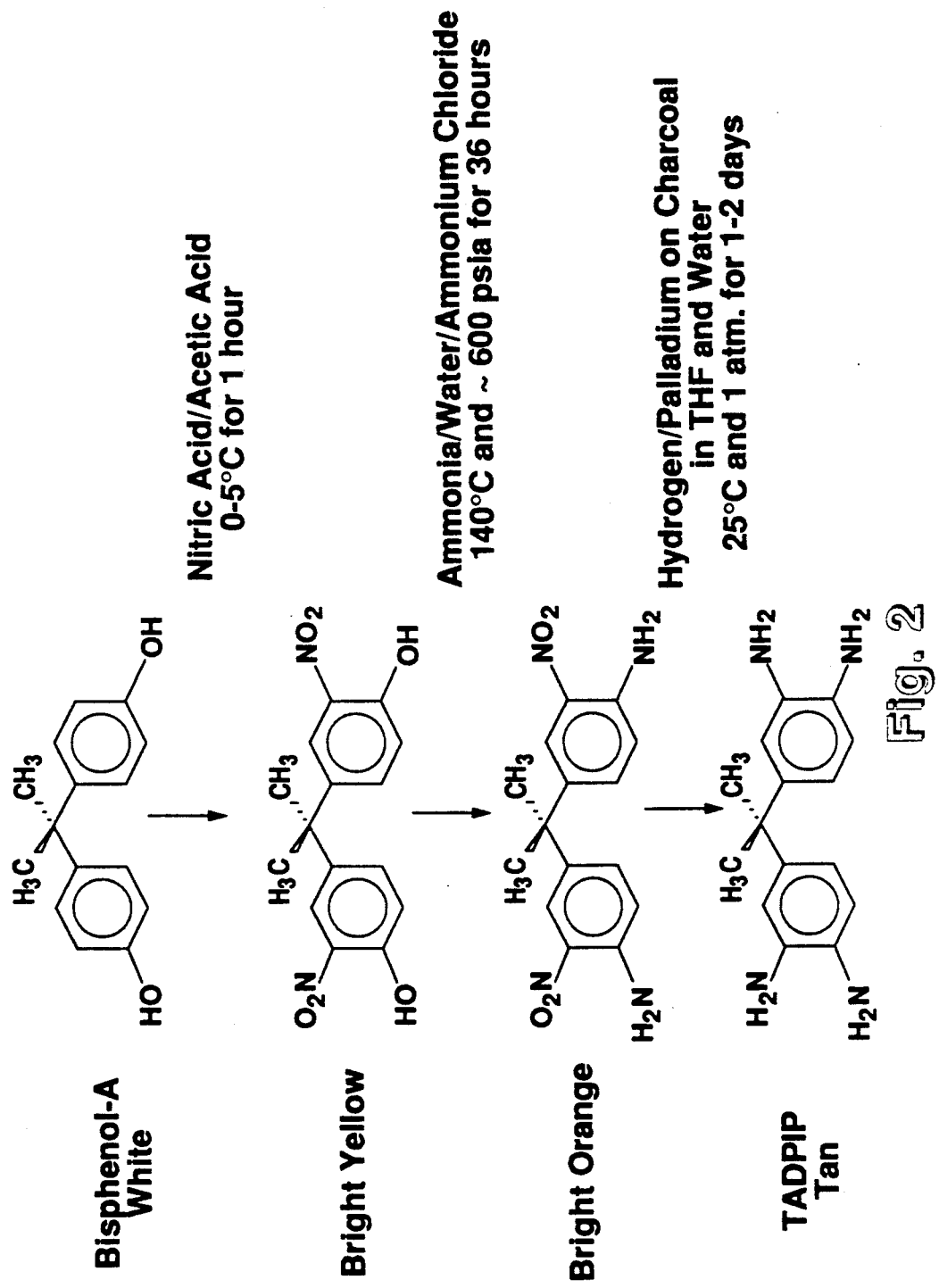
FIG. 2 shows the synthesis of TADPIP from bisphenol-A.

The synthesis of TADPIP from bisphenol-A is shown in FIG. 2 and was accomplished by the nitration of bisphenol-A, followed by a nucleophilic exchange which replaces the hydroxy groups with amino groups, and finally the reduction of the nitro groups to amino groups. The order of these reactions is important since the nitro groups activate the bisphenol-A towards the aromatic nucleophilic substitution. Elemental analysis and proton NMR were used to verify the composition of the products and the placement of substituents.

Bisphenol-A was nitrated by the procedure of Bailar, 1958, 1959. In a round bottom 1000 ml flask with a stir bar was placed 150 grams of bisphenol-A and 500 ml of acetic acid. The mixture was stirred to give a solution while chilled with a bath of ice-water. A dropping funnel was used to add 150 ml of reagent grade nitric acid to the solution so that the reaction temperature stayed at 0°–5° C. After the nitric acid addition was complete, the mixture was stirred for one hour at 0°–50° C., allowed to warm to room temperature, and stirred for one hour. The mixture was poured into 2 liters of crushed ice and filtered. The bright yellow product was purified by vacuum sublimation followed by recrystallization from 2 liters of 19:1 ethanol and methyl ethyl ketone. The yield after purification was 142 grams (68%) of bright yellow 2,2-bis(3-nitro-4-hydroxyphenyl)propane melting at 133°–136° C.

The 2,2-bis(3-nitro-4-hydroxyphenyl)propane was aminated using a procedure for the production of meta-nitro-para-toluidine from meta-nitro-paracresol (Cryer). A stainless steel reaction vessel was designed for this reaction. The vessel had a capacity of 200 ml which made the scale of the reaction convenient. The side wall and flanges were ½" thick and the bottom 1" thick for a large margin of safety. A heating tape and variable transformer were used to heat the vessel. The temperature within the vessel was calibrated against the transformer setting by heating water within the vessel and monitoring the temperature with a thermocouple.

A typical run consisted of charging the reactor with 35 grams of 2,2-bis(3-nitro-4-hydroxyphenyl)propane, 20 grams of ammonium chloride, 40 ml of water and a stirring bar. The vessel was capped and placed in a −70° C. freezer overnight to freeze the contents. Ammonia was condensed into a 100 ml flask until 63 ml had been collected. The ammonia was added to the reaction vessel and the vessel bolted shut. A variable transformer and heating tape were used to heat the contents to 140° C. for 30 hours and a stirring plate was used to keep the reaction well mixed. The vessel was then allowed to cool to room temperature and vented to release the excess ammonia. The contents were slurried with 500 ml of 1 molar sodium hydroxide solution to dissolve the unreacted starting materials. The slurry was filtered, washed with distilled water, and dried. Recrystallization from toluene and vacuum sublimation gave 32.5 grams (93%) of orange 2,2-bis(3-nitro-4-aminophenyl)-propane melting at 207°–210° C. Several runs of the amination reaction were completed to produce enough material for the reduction step. Analysis calculated for $C_{15}H_{16}N_4O_4$: C, 56.96%; H, 5.10%; N, 17.71%; O, 20.23%. Found: C, 57.06%; H, 5.23%; N, 17.48%; O, 20.28%.

The 2,2-bis(3-nitro-4-aminophenyl)propane was converted to TADPIP by catalytic reduction of the nitro groups to amino groups using 0.2 mole-% palladium on charcoal and hydrogen. The method of palladium on charcoal was chosen since the product obtained was easily separated from the catalyst, whereas the method of hydrochloric acid and iron may cause contamination by inorganic salts. A mixture of 400 ml tetrahydrofuran and 100 ml of water was used as the solvent. A blanket of hydrogen was maintained at slightly greater than atmospheric pressure by means of a mercury bubbler. The mixture of tetrahydrofuran, water, the dinitro compound, and the catalyst was stirred rapidly to ensure efficient mass transfer. Two means were used to monitor the progress of the reaction. First, the color changed from orange to colorless as the reaction approached completion. Secondly, the hydrogen uptake slowed as the reaction proceeded and could be checked by observing the rise of the mercury within the bubbler after shutting off the hydrogen source. The tetrahydrofuran was distilled until the boiling point of the solution was 100° C. and water added to give a slurry of 500 ml water, catalyst, and product. The slurry was allowed to cool and was filtered to remove the catalyst. The TADPIP was purified by sublimation three times at 140° C. and 0.1 mm Hg to give orangish-white crystals melting at 147.5°–149.5° C.

EXAMPLE 2

The Synthesis of 6FTA Monomer

Figure 4:
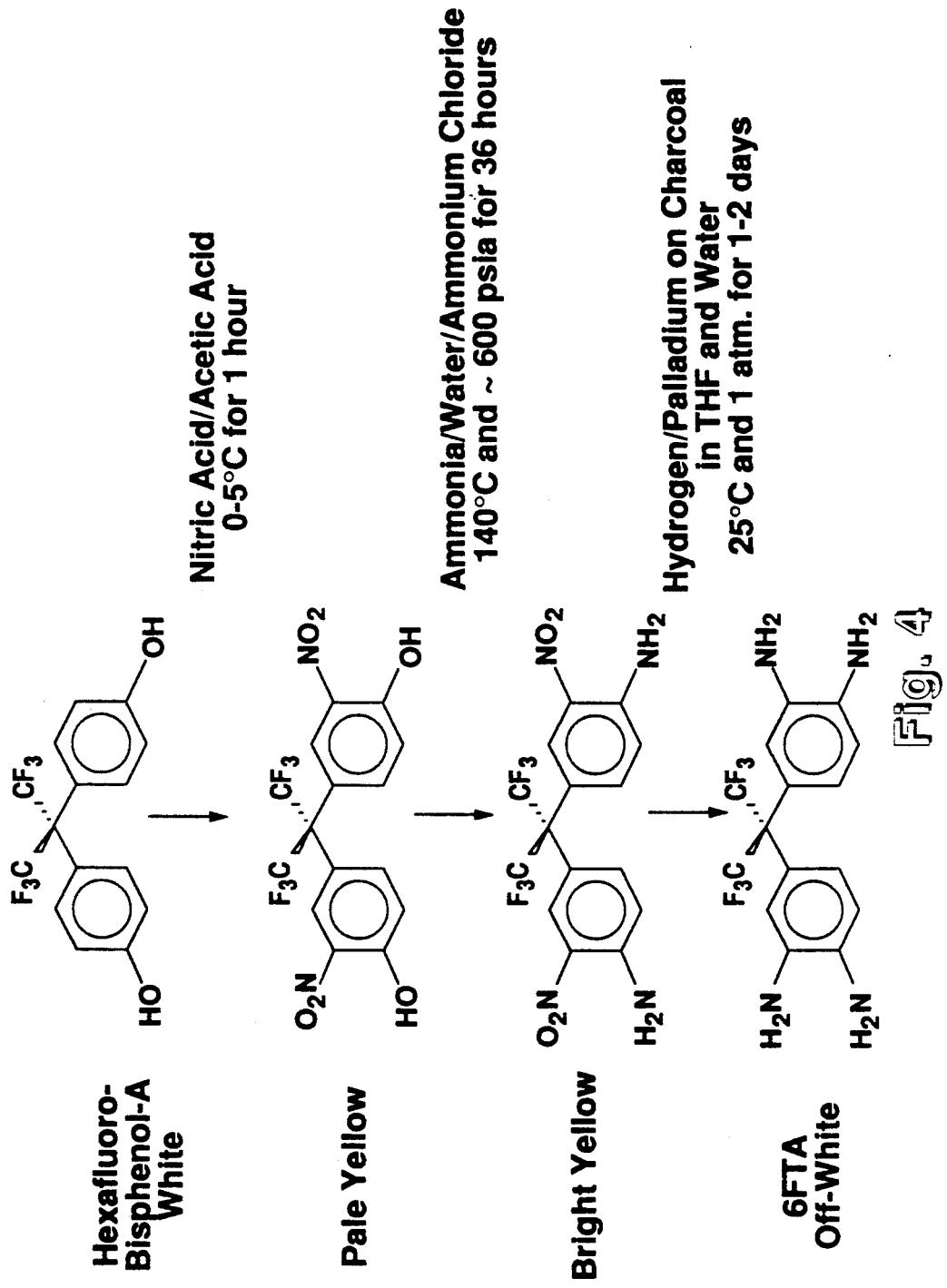
FIG. 4 shows the synthesis of 6FTA from hexafluoro-bisphenol-A.

The hexafluorinated tetraamine 6FTA is the TADPIP structure with all the hydrogens of the isopropylidene connector replaced with fluorines. The 6FTA was synthesized from hexafluoro-bisphenol-A just as the TADPIP was synthesized from bisphenol-A. The synthetic scheme is shown in FIG. 4.

In a ID-1000 ml round bottom flask was placed a stir bar, 100 grams of hexafluorobisphenol-A and 400 ml of acetic acid. The mixture was stirred to give a solution while chilled with a bath of ice-water. A dropping funnel was used to add 40 ml of reagent grade nitric acid to the solution dropwise so that the reaction temperature stayed at 0°–5° C. After the nitric acid addition was complete, the mixture was stirred for an additional hour at 0°–5° C., allowed to warm to room temperature, and stirred at room temperature for one hour. The mixture was poured into 2 liters of crushed ice and filtered. The dark yellow product was sublimed to give pale yellow crystals of 2,2-bis(3-nitro-4-hydroxyphenyl)-1, 1,1,3,3,3-hexafluoropropane melting at 119°–122° C.

The 2,2-bis(3-nitro-4-hydroxyphenyl)-1,1,1,3,3,3-hexafluoropropane was aminated using a procedure for the production of m-$NO_2$-p-toluidine from m-$NO_2$-p- cresol (Cryer). Into a 316 stainless steel reaction vessel with a capacity of 200 ml were placed 35 grams of 2,2-bis(3-nitro-4-hydroxyphenyl)-1, 1,1,3,3,3-hexafluoropropane, 15 grams of ammonium chloride, 30 ml of water and a stirring bar. The vessel was capped and placed in a −70° C. freezer overnight to freeze the contents. Ammonia was condensed into a 100 ml flask until 47 ml had been collected. The ammonia was added to the reaction vessel and the vessel bolted shut. A variable transformer and heating tape were used to heat the contents to 140° C. for 30 hours and a stirring plate was used to keep the reaction well mixed. The vessel was then allowed to cool to room temperature and vented to release the excess ammonia. The contents were slurried with 500 ml of 1 molar sodium hydroxide solution to dissolve the unreacted starting materials. The slurry was filtered, washed with distilled water, and dried to give a brown solid. Recrystallization from a 50/50 mixture of ethanol and ethyl acetate gave 31 grams (89% yield) of yellow solid melting at 278°–281° C. Analysis calculated for $C_{15}H_{10}F_6N_4O_4$: C, 42.47%; H, 2.38%; F, 26.76%; N, 13.21%; O, 15.08%. Found: C, 42.36%; H, 2.62%; F, 26.36%; N, 12.95%; O, 15.714.

The 2,2-bis(3-nitro-4-aminophenyl)-1,1,1,3,3,3-hexafluoropropane was converted to 6FTA by catalytic reduction of the nitro groups to amino groups using 0.2 mole-% palladium on charcoal and hydrogen in a manner similar to the TADPIP synthesis. Purification of the 6FTA by three sublimations at 200°–210° C. and 0.1 mmhg gave orange-yellow crystals melting at 218°–221° C.

EXAMPLE 3

The Polyamide and Polypyrrolone of 6FDA-TABP

This example provides the synthesis and fluid separation properties of the polyamide form and polypyrrolone membrane form of 6FDA-TABP.

TABP has one rotatable bond between the phenyl rings whereas TADPO with its ether linkage has two rotatable bonds as shown in the following structures:

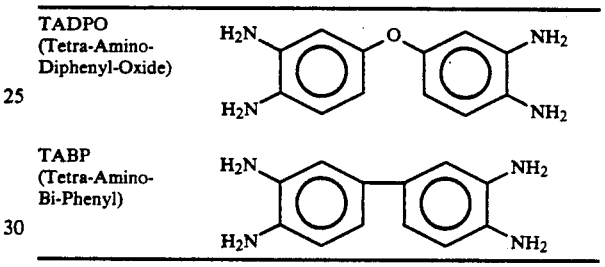

| TADPO (Tetra-Amino-Diphenyl-Oxide) | |
| TABP (Tetra-Amino-Bi-Phenyl) | |

Synthesis of the polypyrrolone followed a modified procedure of Foster et al. (1965) and is depicted in FIG. 1.

The polymerization was carried out under an argon blanket with Aldrich Chemical Co. brand anhydrous grade N,N-dimethylacetamide (DMAC) packaged in SureSeale bottles. The 6FDA was purchased from ChrisKev and was purified by sublimation three times at 220°–230° C. and 0.1 mmhg prior to use. The TABP was purchased from Aldrich Chemical Co. and was purified by sublimation three times at 165°–170° C. and 0.1 mmhg prior to use. The glassware and 3A and 4A molecular sieves used were dried in a vacuum oven overnight at 200° C. The glassware was assembled hot while argon was passed through the glassware. After assembly, the glassware was flamed with a torch. The monomers were then placed in a vacuura oven and dried overnight at 100° C. and 0.1 mmhg overnight to remove surface moisture from the crystals. Transfer needles with Teflon tubing were used for all liquid manipulations to minimize the contact of the hygroscopic DMAC with atmospheric moisture. A positive pressure of argon was applied to the source of a liquid to force the liquid through the transfer needle. A needle attached to an oil bubbler was pierced through septum of flask to which the liquid was transferred so as to prevent any pressure buildup in the glassware. The polymerization flask was 500 ml flask with 3 necks; a rubber septum over one side, a 125 ml addition funnel capped with a rubber septum on the other side, and an Ace Glass stir shaft, an Ace Glass stir bearing, and a Teflon stir blade in the center neck.

TABP (8.135 grams, 39.97 mmoles) was added to a 125 al flask with a stir bar and capped with a rubber septum. 6FDA (16.865 grams, 39.97 mmoles) was placed in a 125 ml flask with a stir bar and covered with a rubber septum. The DMAC (800 ml) was transferred from the bottle to a 1000 ml flask with 3A and 4A molecular sieves and capped with a rubber septum to insure dryness. Approximately 50 ml of DMAC was transferred to the TABP flask and the 6FDA flask. The contents of the TABP and 6FDA flasks were stirred to give transparent solutions. The TABP solution (amber in color) was then transferred to the reaction flask and the 6FDA solution (slightly straw colored) was transferred to the addition funnel. The flasks used for forming the solutions were then rinsed twice with 25 ml portions of DMAC; the TABP rinsings added to the reaction flask and the 6FDA rinsings added to the addition funnel. Another 100 ml of DMAC was added to the reaction flask so that the solids contents was approximately 5%.

The stir shaft motor was started and the 6FDA solution added at a rate of approximately 15 drops per minute. After the 6FDA solution had been added to the reaction flask, more DMAC was added to the reaction mixture through the addition funnel to dilute the polymer solution to 54 solids. The rinsing of the addition funnel insured stoichiometry was maintained which is important for forming high molecular weight. The dilution of the reaction mixture helped insure the formation of a linear, not crosslinked, polymer. After all additions were complete, the polymer solution was stirred overnight. The next morning the stirring was stopped and the solution filtered through a 2000Å Teflon filter (Aldrich) to remove particulates and gel fragments which could cause defects in the film formation.

Glass could not be used for a casting surface for the films. The glass surfaces were damaged by the simultaneous shrinkage and adhesion of the films to the glass, resulting in the tearing of the glass surface. Teflon dishes 3.5" in diameter, $\frac{1}{4}$" deep, and $\frac{3}{4}$" thick served as a mold for the films. The molds were placed on an aluminum platen and leveled; the aluminum platen was heated with a hot plate so that the top surface of the Teflon dish was at a temperature of 50° C. A glass funnel served as a dust cover and controlled the rate of evaporation. Evaporation of the solvent overnight gave films which were rigid and could be removed easily from the mold. By varying the volume of solution placed in the mold from 20 to 30 ml, film thicknesses varied between 100 and 150 microns. The films after removal from the Teflon dish were in the polyamide form and were dried of residual solvent. The solvent was removed by drying in a vacuum oven for 3 days at 100° C. at 0.1 mmHg. Conversion of the polyamide films to polypyrrolone films was accomplished by progressively heating the films to 285° C. over a 2 day period under a vacuum of 0.1 mmHg. The films were rigid and could not be creased without cracking and were transparent and amber in color.

Tables 11-14 present permeabilities, solubilities, diffusivities, glass transition temperatures and fractional free volumes for 6FDA-TABP compared to the known polymer, 6FDA-TADPO.

TABLE 11

Pure Gas Permeabilities and Ideal Permselectivities

| | Permeability (barrers[a] at 35° C.) | | | Ideal permselectivity (at 35° C.) | | |
|---|---|---|---|---|---|---|
| Polymer | He 10 atm | $O_2$ 3 atm | $CO_2$ 10 atm | He/$CH_4$ 10 atm | $O_2/N_2$ 3 atm | $CO_2$/$CH_4$ 10 atm |
| 6FDA-TABP | | | | | | |

TABLE 11-continued

Pure Gas Permeabilities and Ideal Permselectivities

| | Permeability (barrers[a] at 35° C.) | | | Ideal permselectivity (at 35° C.) | | |
|---|---|---|---|---|---|---|
| Polymer | He 10 atm | $O_2$ 3 atm | $CO_2$ 10 atm | He/$CH_4$ 10 atm | $O_2/N_2$ 3 atm | $CO_2$/$CH_4$ 10 atm |
| Polyamide | 13.9 | 0.69 | 2.75 | 215.4 | 6.2 | 42.7 |
| Pyrrolone | 138.0 | 16.4 | 63.6 | 100.2 | 5.5 | 46.2 |
| 6FDA-TADPO | | | | | | |
| Polyamide | 19.1 | 0.97 | 3.69 | 230.9 | 5.8 | 44.5 |
| Pyrrolone | 90.2 | 7.9 | 27.4 | 171.5 | 6.5 | 52.2 |

[a] barrer = $10^{-10} \left[ \frac{cm^3(STP) - cm}{cm^2 - sec - cmHg} \right]$

TABLE 12

Pure Gas Solubilities and Solubility Selectivities

| | Solubility[a] | | | Solubility selectivities | | |
|---|---|---|---|---|---|---|
| Polymer | He | $O_2$ | $CO_2$ | He/$CH_4$ | $O_2/N_2$ | $CO_2$/$CH_4$ |
| 6FDA-TABP | | | | | | |
| Polyamide | 0.030 | 0.30 | 2.49 | 0.058 | 1.41 | 4.74 |
| 6FDA-TADPO | | | | | | |
| Polyamide | 0.067 | 0.55 | 3.06 | 0.085 | 1.46 | 3.87 |
| Pyrrolone | 0.103 | 1.09 | 4.65 | 0.060 | 1.16 | 2.71 |

[a] $\frac{cc(STP)}{cc \ atm}$

TABLE 13

Pure Gas Diffusivities and Diffusivity Selectivities

| | Diffusivity[a] | | | Diffusivity selectivity | | |
|---|---|---|---|---|---|---|
| Polymer | He | $O_2$ | $CO_2$ | He/$CH_4$ | $O_2/N_2$ | $CO_2$/$CH_4$ |
| 6FDA-TABP | | | | | | |
| Polyamide | 34800 | 173 | 84 | 3731 | 4.39 | 9.01 |
| 6FDA-TADPO | | | | | | |
| Polyamide | 21600 | 135 | 92 | 2708 | 4.01 | 11.5 |
| Pyrrolone | 66500 | 549 | 448 | 2858 | 5.6 | 19.3 |

[a] $\frac{10^{-10} cm^2}{sec}$

TABLE 14

Glass Transition Temperatures and Fractional Free Volumes of the 6FDA-TADPO and 6FDA-TABP Polypyrrolones and Polyamides.

| Polymer | Glass Transition Tg, °C. | Fractional Free Volme |
|---|---|---|
| Properties of the Polypyrrolones. | | |
| 6FDA-TADPO | ~375 | 0.1956 |
| 6FDA-TABP | ~370 | 0.1889 |
| Properties of the Polyamides. | | |
| 6FDA-TADPO | Ring Closure | 0.1476 |
| 6FDA-TABP | Ring Closure | 0.1496 |

The 6FDA-TABP polypyrrolone is, with the exception of helium, twice as permeable as the 6FDA-TADPO polypyrrolone. The selectivities of the 6FDA-TABP are somewhat lower than the 6FDA-TADPO. This permeability enhancement could prove useful in applications where high permeabilities are required such as: 85% nitrogen or 25% oxygen production from air, hydrogen recovery where concentration driving force is a factor, and applications where module weight is a concern as on vehicles. The 6FDA-TABP polypyrrolone permeabilities are similar to the 6FDA-6F$_p$DA polyimide, but the selectivities of the 6FDA-TABP are greater than the 6FDA-6F$_p$DA polyimide.

Samples of the polypyrrolones tested were insoluble in all organic solvents tried, including the polymerization solvent, DMAC, used for the synthesis of the precursor polyamide. Since the polypyrrolone was insoluble, no direct means of molecular weight determination was possible. The molecular mass of the polyamide solutions could be determined relative to polystyrene by gel-permeation chromatography. Light scattering measurements of the polyamide solutions along with the measurement of the variation of the index of refraction as a function of concentration would give an absolute measurement of the weight average molecular mass.

EXAMPLE 4

The Polypyrrolone of 6FDA-TADPIP

This example provides the synthesis and fluid separation properties of the polypyrrolone membrane form of 6FDA-TADPIP.

TADPIP has an isopropylidene linkage rather than the ether linkage present in TADPO. This variation was intended to inhibit packing and intrasegmental motion, thus simultaneously increasing permeability and permselectivity. The TADPIP and TADPO structures are as follows:

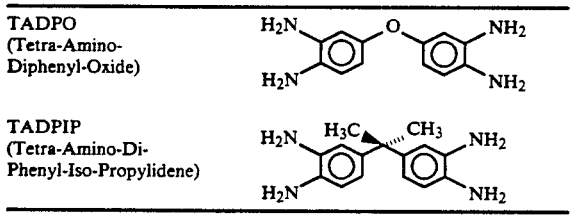

TADPO (Tetra-Amino-Diphenyl-Oxide)

TADPIP (Tetra-Amino-Di-Phenyl-Iso-Propylidene)

The monomer TADPIP was synthesized as described in Example

Figure 3:
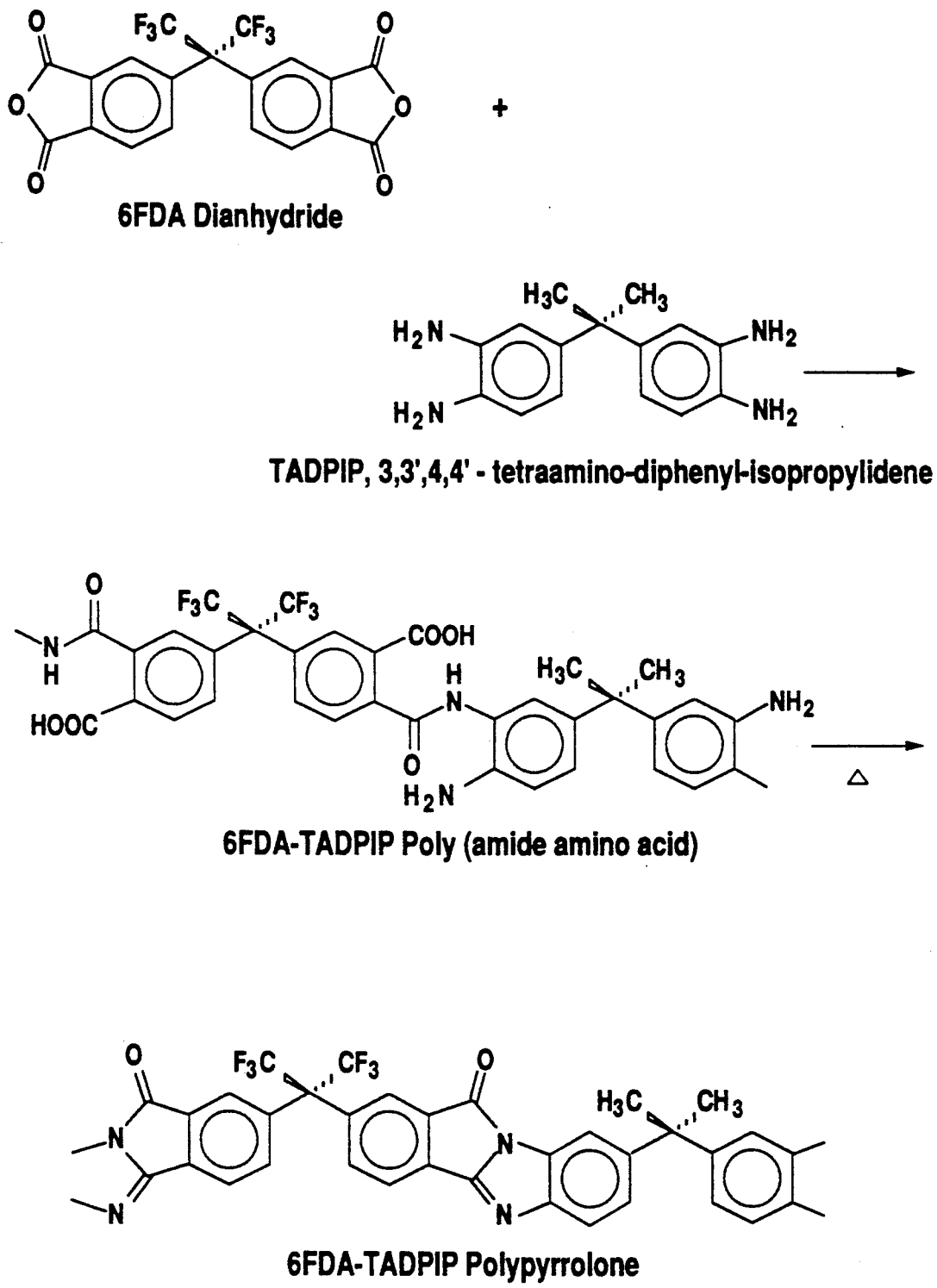
FIG. 3 shows the reaction of 6FDA dianhydride with TADPIP to form the polyamide 6FDA-TADPIP and further thermal conversion to the 6FDA-TADPIP polypyrrolone.

The 6FDA-TADPIP polymer was synthesized using the same procedures as described in example 3 for the synthesis of 6FDA-TABP. The synthetic scheme is presented in FIG. 3. Twenty-five grams of 6FDA-TADPIP polymer was synthesized and films formed. The 6FDA-TADPIP polyamide films were brittle after complete solvent removal. One film was cured to a polypyrrolone form and used for permeation measurements. Smaller fragments of 6FDA-TADPIP polyamide were cured to polypyrrolone form for sorption measurements. The 6FDA-TADPIP polyamide and polypyrrolone films were transparent and amber colored.

Tables 15-18 present permeabilities, solubilities, diffusivities, glass transition temperatures and fractional free volumes for 6FDA-TADPIP compared to the known polymer 6FDA-TADPO.

TABLE 15

Pure Gas Permeabilities and Ideal Permselectivities for Polypyrrolones

| | Permeability (barrers$^a$ at 35° C.) | | | Ideal permselectivity (at 35° C.) | | |
|---|---|---|---|---|---|---|
| Polymer | He 10 atm | O$_2$ 3 atm | CO$_2$ 10 atm | He/ CH$_4$ 10 atm | O$_2$/N$_2$ 3 atm | CO$_2$/ CH$_4$ 10 atm |
| 6FDA-TADPIP | 102.3 | 9.2 | 32.5 | 135.3 | 5.6 | 43.0 |
| 6FDA-TADPO | 90.2 | 7.9 | 27.4 | 171.5 | 6.5 | 52.2 |

TABLE 15-continued

Pure Gas Permeabilities and Ideal Permselectivities for Polypyrrolones

| | Permeability (barrers$^a$ at 35° C.) | | | Ideal permselectivity (at 35° C.) | | |
|---|---|---|---|---|---|---|
| Polymer | He 10 atm | O$_2$ 3 atm | CO$_2$ 10 atm | He/ CH$_4$ 10 atm | O$_2$/N$_2$ 3 atm | CO$_2$/ CH$_4$ 10 atm |

$^a$barrier = $10^{-10} \left[ \dfrac{cm^3(STP) - cm}{cm^2 - sec - cmHg} \right]$

TABLE 16

Pure Gas Solubilities and Solubility Selectivities for Polypyrrolones

| | Solubility$^a$ | | | Solubility selectivities | | |
|---|---|---|---|---|---|---|
| Polymer | He | O$_2$ | CO$_2$ | He/ CH$_4$ | O$_2$/N$_2$ | CO$_2$/CH$_4$ |
| 6FDA-TADPIP | 0.069 | 1.11 | 4.78 | 0.040 | 1.31 | 2.82 |
| 6FDA-TADPO | 0.103 | 1.09 | 4.65 | 0.060 | 1.16 | 2.71 |

$^a$ $\dfrac{cc(STP)}{cc\ atm}$

TABLE 17

Pure Gas Diffusivities and Diffusivity Selectivities

| | Diffusivity$^a$ | | | Diffusivity selectivity | | |
|---|---|---|---|---|---|---|
| Polymer | He | O$_2$ | CO$_2$ | He/CH$_4$ | O$_2$/N$_2$ | CO$_2$/ CH$_4$ |
| 6FDA-TADPIP | 113000 | 629 | 518 | 3342 | 4.3 | 15.3 |
| 6FDA-TADPO | 66500 | 549 | 448 | 2858 | 5.6 | 19.3 |

$^a$ $\dfrac{10^{-10} cm^2}{sec}$

TABLE 18

Glass Transition Temperatures and Fractional Free Volumes of the 6FDA-TADPO and 6FDA-TADPIP polypyrrolones Properties of the Polypyrrolones.

| Polymer | Glass Transition Tg, °C. | Fractional Free Volme |
|---|---|---|
| 6FDA-TADPO | ~375 | 0.1956 |
| 6FDA-TADPIP | ~370 | 0.1910 |

The selectivities of the two polymers are similar, however, the 6FDA-TADPIP polypyrrolone has permeabilities greater than 6FDA-TADPO which is advantageous when permeability rather than selectivity is a determining factor for design. The TADPIP polypyrrolone has a 30% greater helium/methane permselectivity than the IPDA polyimide.

The helium diffusivity of the 6FDA-TADPIP polypyrrolone is greater than the 6FDA-IPDA polyamide by a factor of 2. The solubility of the 6FDA-TADPIP polypyrrolone is similar to the corresponding 6FDA-IPDA and 6FDA-6FpDA polyamides. The result is that the permeability of the 6FDA-TADPIP polypyrrolone is greater than the 6FDA-IPDA and 6FDA-6FpDA polyimides and suffers no plasticization.

The fractional free volume of the 6FDA-TADPIP polypyrrolone is 13% greater than the 6FDA-IPDA and 6FDA-6FpDA polyimides which is significant, and thus the permeability of the polypyrrolone is greater.

No structurally similar polypyrrolone and polyimide pair are known to have similar fractional free volumes.

However, the 6FDA-TADPIP polypyrrolone and the 6FDA-6FpDA polyimide do have similar fractional free volumes. The structural difference besides the polymer type is that the 6FDA-TADPIP polypyrrolone has an isopropylidene and a hexafluorisopropylidene linkage whereas the 6FDA-6FpDA polyimide has two hexafluorisopropylidene linkages. The result is that the 6FDA-TADPIP polypyrrolone has greater diffusivity selectivities (up to a factor of 2) and thus greater permselectivities (up to 604) than the 6FDA-6FpDA polyimide. These results support the argument that the polypyrrolones are indeed more rigid than the polyimides and thus are resistant to plasticization.

EXAMPLE 5

THE POLYPYRROLONE OF 6FDA-6FTA

Figure 5:
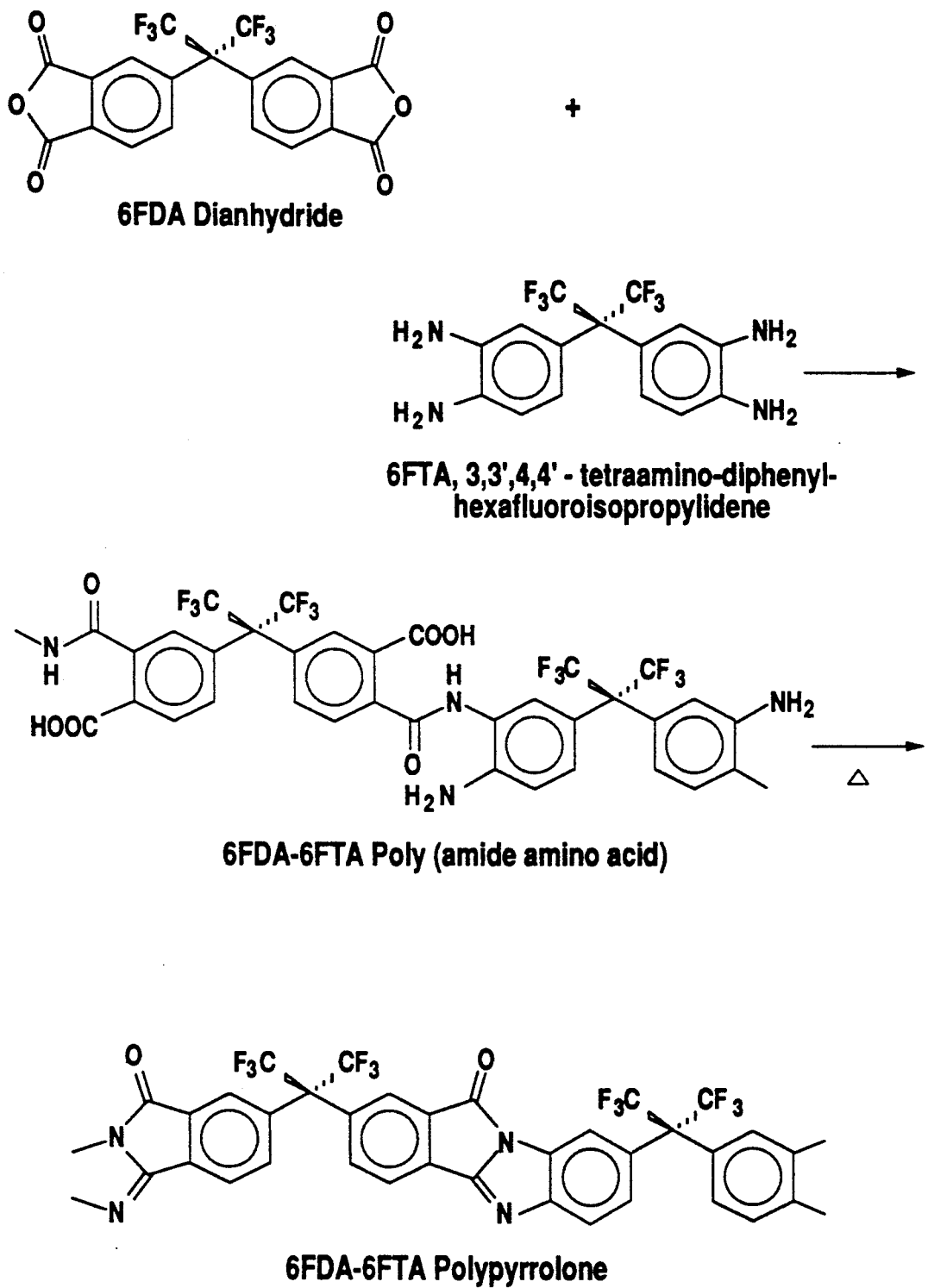
FIG. 5 shows the reaction of 6FDA dianhydride with 6FTA to form the polyamide 6FDA-6FTA and further thermal conversion to the 6FDA-6FTA polypyrrolone.

In a similar manner to the synthesis of 6FDA-TABP described in example 3, 25 grams of 6FDA-6FTA polymer was synthesized as shown in FIG. 5. Five 6FDA-6FTA polyamide films which were bright yellow in color were cast and dried. The 6FDA-6FTA polyamide films were tougher than the 6FDA-TADPIP films, and were cured to polypyrrolone form for use in sorption and permeation measurements. The 6FDA-6FTA polypyrrolone films were more brightly colored than the 6FDA-6FTA polyamide films. Tables 19–22 present the permeabilities, solubilities, diffusivities, glass transition temperatures and fractional free volumes of 6FDA-6FTA compared to the known polymer 6FDA-TADPO.

TABLE 19

Pure Gas Permeabilities and Ideal Permselectivities for Polypyrrolones

| Polymer | Permeability (barriers$^a$ at 35° C.) | | | Ideal permselectivity (at 35° C.) | | |
|---|---|---|---|---|---|---|
| | He 10 atm | $O_2$ 3 atm | $CO_2$ 10 atm | He/$CH_4$ 10 atm | $O_2/N_2$ 3 atm | $CO_2/CH_4$ 10 atm |
| 6FDA-6FTA | 267.3 | 41.2 | 138.5 | 65.9 | 4.7 | 34.1 |
| 6-FDA-TADPO | 90.2 | 7.9 | 27.4 | 171.5 | 6.5 | 52.2 |

$^a$barrier = $10^{-10} \left[ \dfrac{cm^3(STP) - cm}{cm^2 - sec - cmHg} \right]$

TABLE 20

Pure Gas Solubilities and Solubility Selectivities for Polypyrrolones

| Polymer | Solubility$^a$ | | | Solubility selectivities | | |
|---|---|---|---|---|---|---|
| | He | $O_2$ | $CO_2$ | He/$CH_4$ | $O_2/N_2$ | $CO_2/CH_4$ |
| 6FDA-6FTA | 0.104 | 1.31 | 5.23 | 0.056 | 1.24 | 2.82 |
| 6FDA-TADPO | 0.103 | 1.09 | 4.65 | 0.060 | 1.16 | 2.71 |

$^a \dfrac{cc(STP)}{cc \, atm}$

TABLE 21

Pure Gas Diffusivities and Diffusivity Selectivities for Polypyrrolones

| Polymer | Diffusivity$^a$ | | | Diffusivity selectivity | | |
|---|---|---|---|---|---|---|
| | He | $O_2$ | $CO_2$ | He/$CH_4$ | $O_2/N_2$ | $CO_2/CH_4$ |
| 6FDA-6FTA | 195000 | 2394 | 2012 | 1176 | 3.78 | 12.1 |
| 6FDA-TADPO | 66500 | 549 | 448 | 2858 | 5.6 | 19.3 |

$^a \dfrac{10^{-10} cm^2}{sec}$

TABLE 22

Glass Transition Temperatures and Fractional Free Volumes of the 6FDA-TADPO and 6FDA-6FTA polypyrrolones.

Properties of the Polypyrrolones.

| Polymer | Glass Transition Tg, °C. | Fractional Free Volme |
|---|---|---|
| 6FDA-TADPO | ~375 | 0.1956 |
| 6FDA-6FTA | ~410 | 0.2144 |

The diffusivities of the 6FDA-6FTA polypyrrolone are greater than the 6FDA-6pDA polyimide by a factor of 1.3 for Helium and 2.5 for $CO_2$. The solubility of the 6FDA-6FTA polypyrrolone is similar to the corresponding 6FDA-IPDA and 6FDA-6pDA polyimides. The result is that the permeability of the 6FDA-6FTA polypyrrolones is greater than the 6FDA-IPDA and 6FDA-6pDA polyimides and suffer no plasticization.

The fractional free volume of the 6FDA-6FTA polypyrrolones is 13% greater than the 6FDA-IPDA and 6FDA-6FpDA polyimides which is significant, and thus the permeability of the polypyrrolone is greater.

Figure 8:
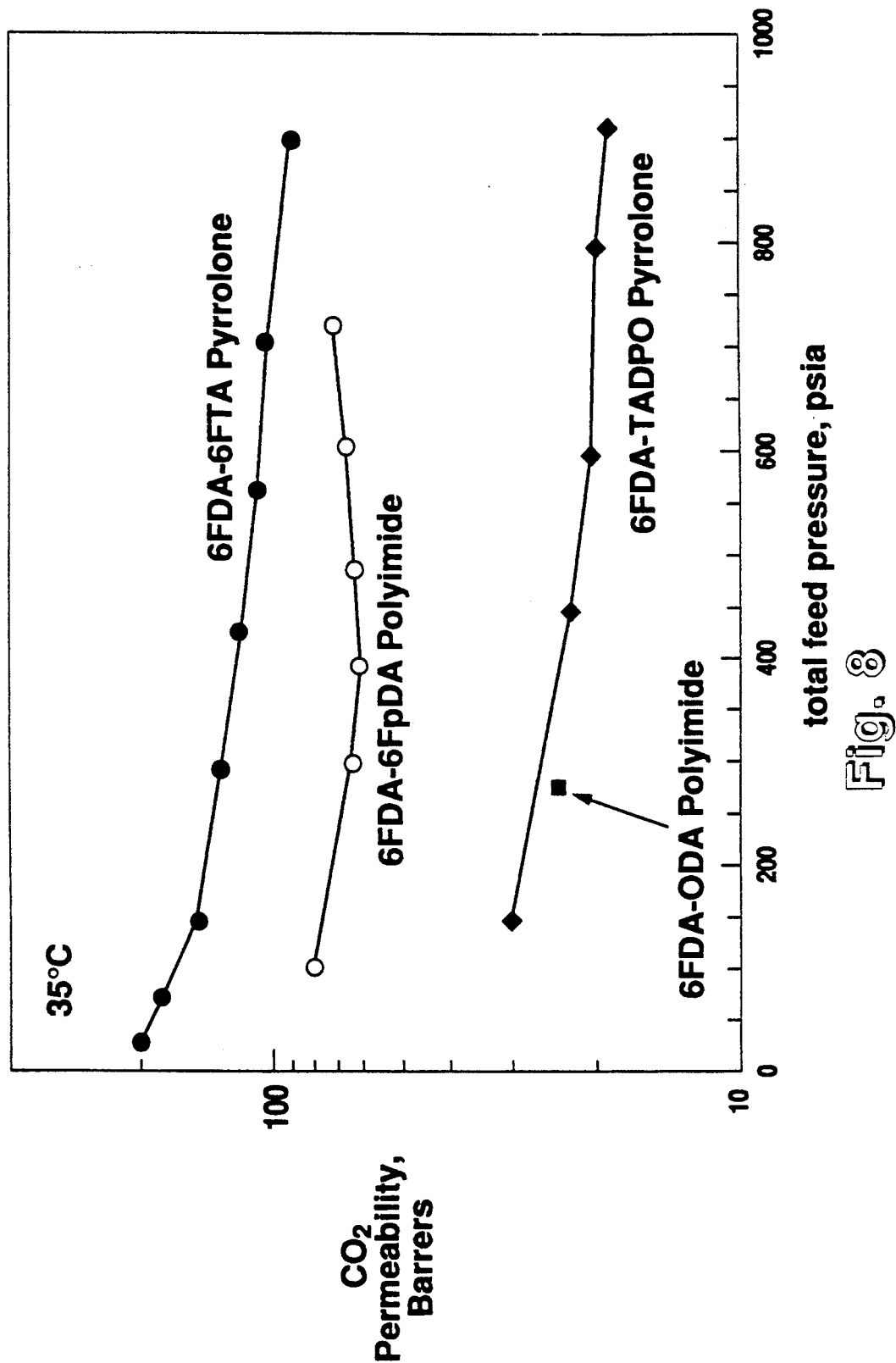
FIG. 8 shows $CO_2$ permeability with a 50:50 $CO_2/CH_4$ feed mixture for various polyimides and polypyrrolones.
Figure 9:
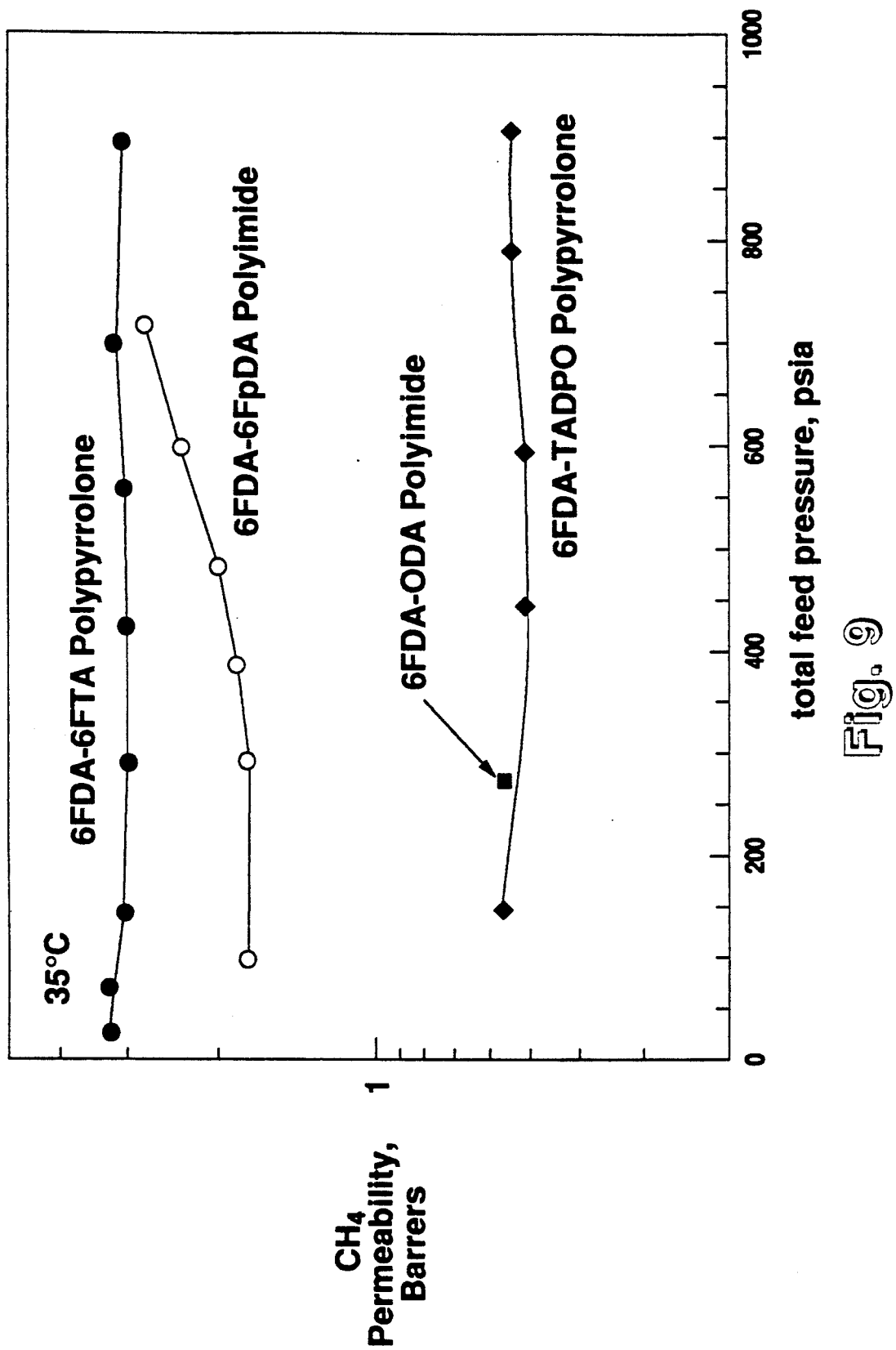
FIG. 9 shows $CH_4$ permeability with a 50:50 $CO_2/CH_4$ feed mixture for various polyimides and polypyrrolones.
Figure 10:
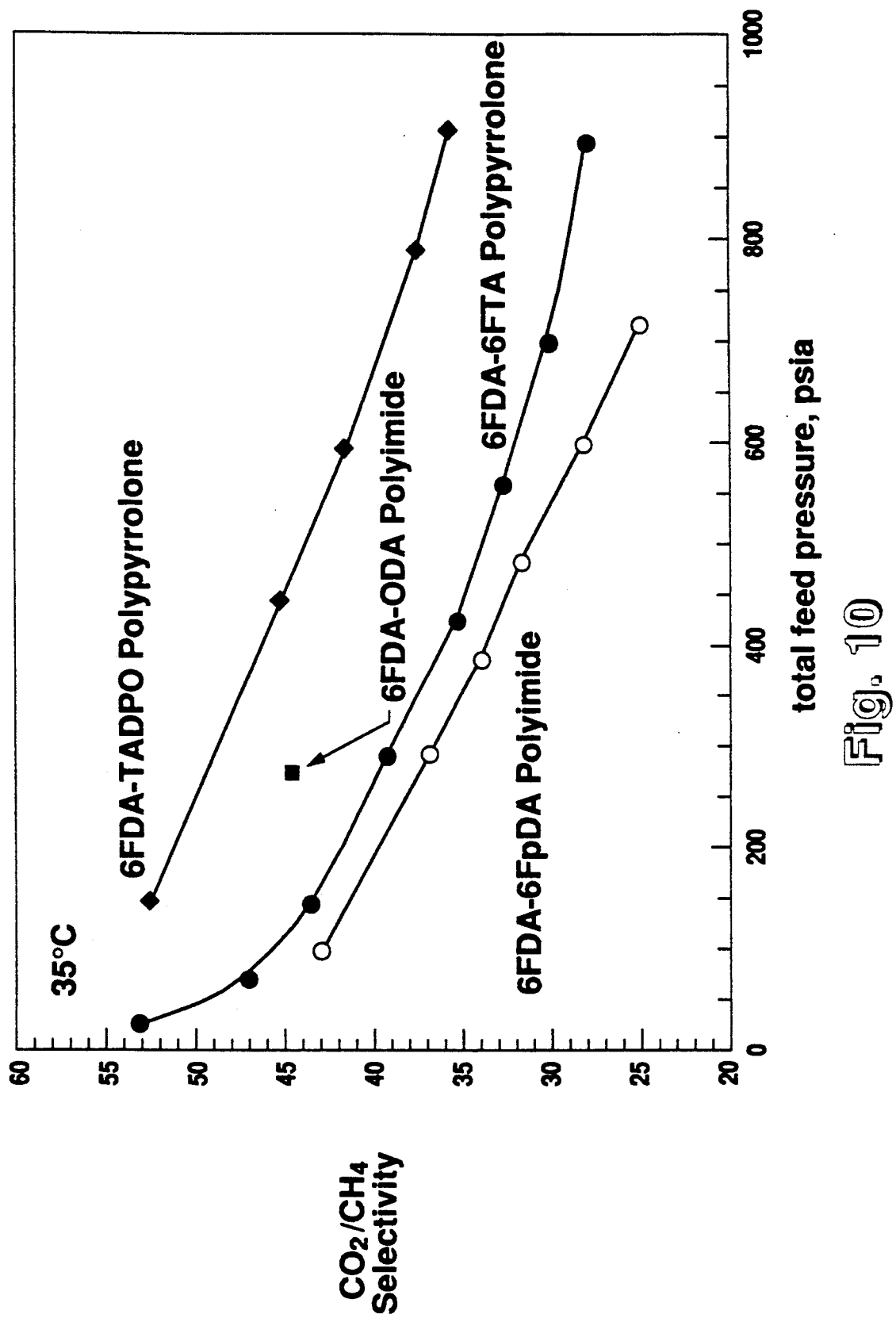
FIG. 10 shows the $CO_2/CH_4$ selectivity with a 50:50 $CO_2/CH_4$ feed mixture for various polyimides and polypyrrolones.

The permselectivity of the 6FDA-6FTA polypyrrolone decreases as the feed pressure of 50:50 $CO_2/CH_4$ mixture is increased, but the rate of the decrease slows as the total feed pressure approaches 1000 psia (FIGS. 8 and 9). The 6FDA-6FpDA polyimide shows a similar decrease in selectivity through the middle pressure range, but the rate of decrease in selectivity never appears to level off. The difference between these two polymers is shown by the diverging curves in FIG. 10 of permselectivity as a function of total feed pressure.

Evidence that the 6FDA-6FTA polypyrrolone undergoes no plasticization but that the 6FDA-6FpDA polyimide does undergo plasticization is shown in the plot of $CO_2$ permeability with a 50:50 $CO_2/CH_4$ mixed feed (FIG. 8). The $CO_2$ permeability of the 6FDA-6FpDA polyimide actually increases with increasing pressure, whereas the 6FDA-6FTA polypyrrolone shows no such increase. The $CH_4$ permeability of the 6FDA-6FpDA polyimide also increases significantly as the feed pressure is increased, thus contributing to the permselectivity decrease (FIG. 9). The $CH_4$ permeability of the 6FDA-6FTA polypyrrolone shows little change as the feed pressure is increased. In an application where $CO_2$ is separated from $CH_4$, less $CH_4$ would be lost and the higher purity $CO_2$ would be produced by using a membrane made from 6FDA-6FTA rather than 6FDA-6FpDA. The decrease in permselectivity of the 6FDA-6FTA polypyrrolone is not due to plasticization since the permeability of neither the $CO_2$ or the $CH_4$ increases as the total feed pressure increases. The 6FDA-6FTA polypyrrolone is plasticization resistant due to the more rigid repeat unit which contains no freely rotatable bonds.

Figure 6:
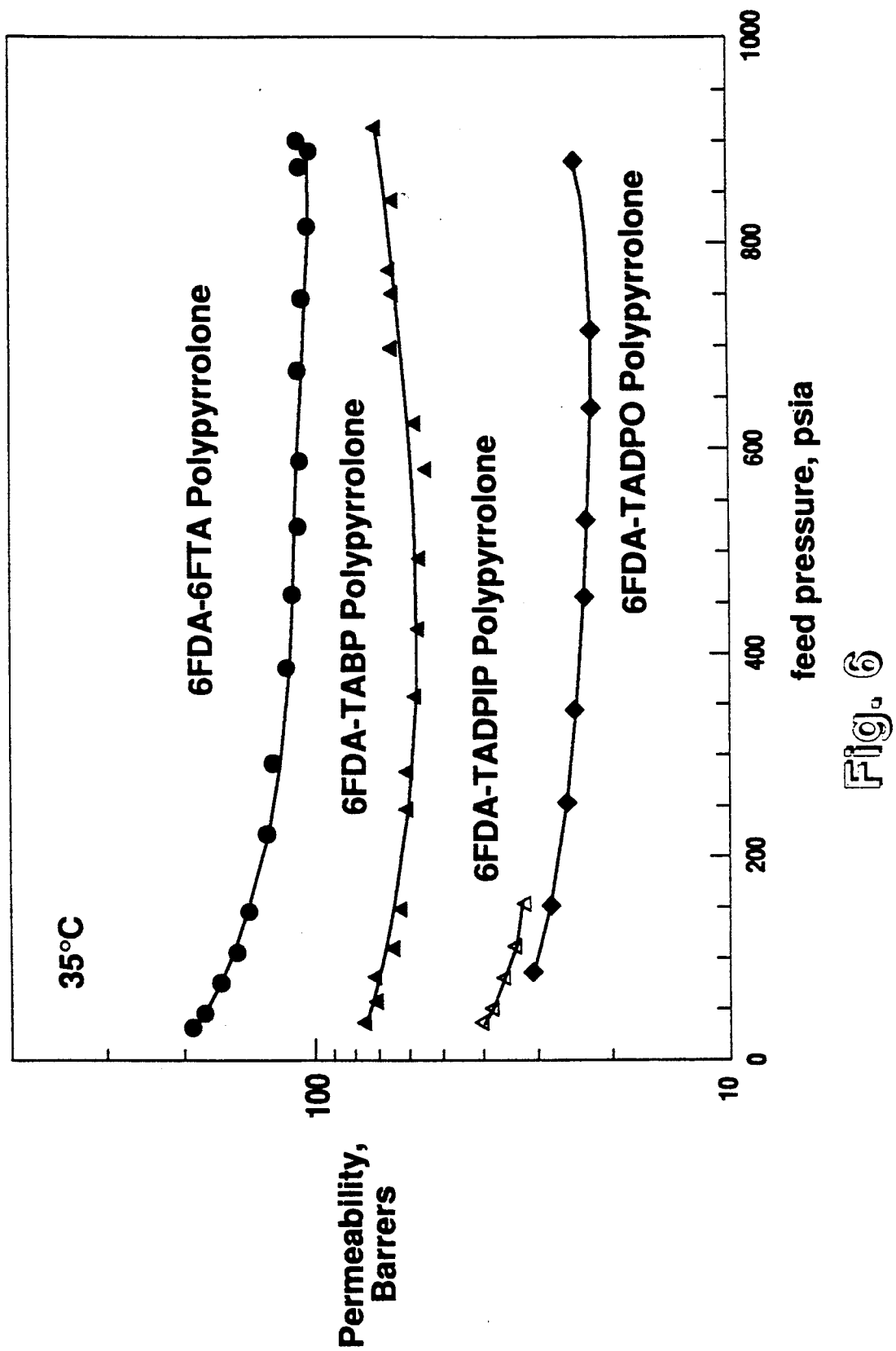
FIG. 6 demonstrates the pure gas $CO_2$ permeabilities with increasing feed pressure of the polypyrrolones of the present invention compared to the 6FDA-TADPO polypyrrolone.
Figure 7:
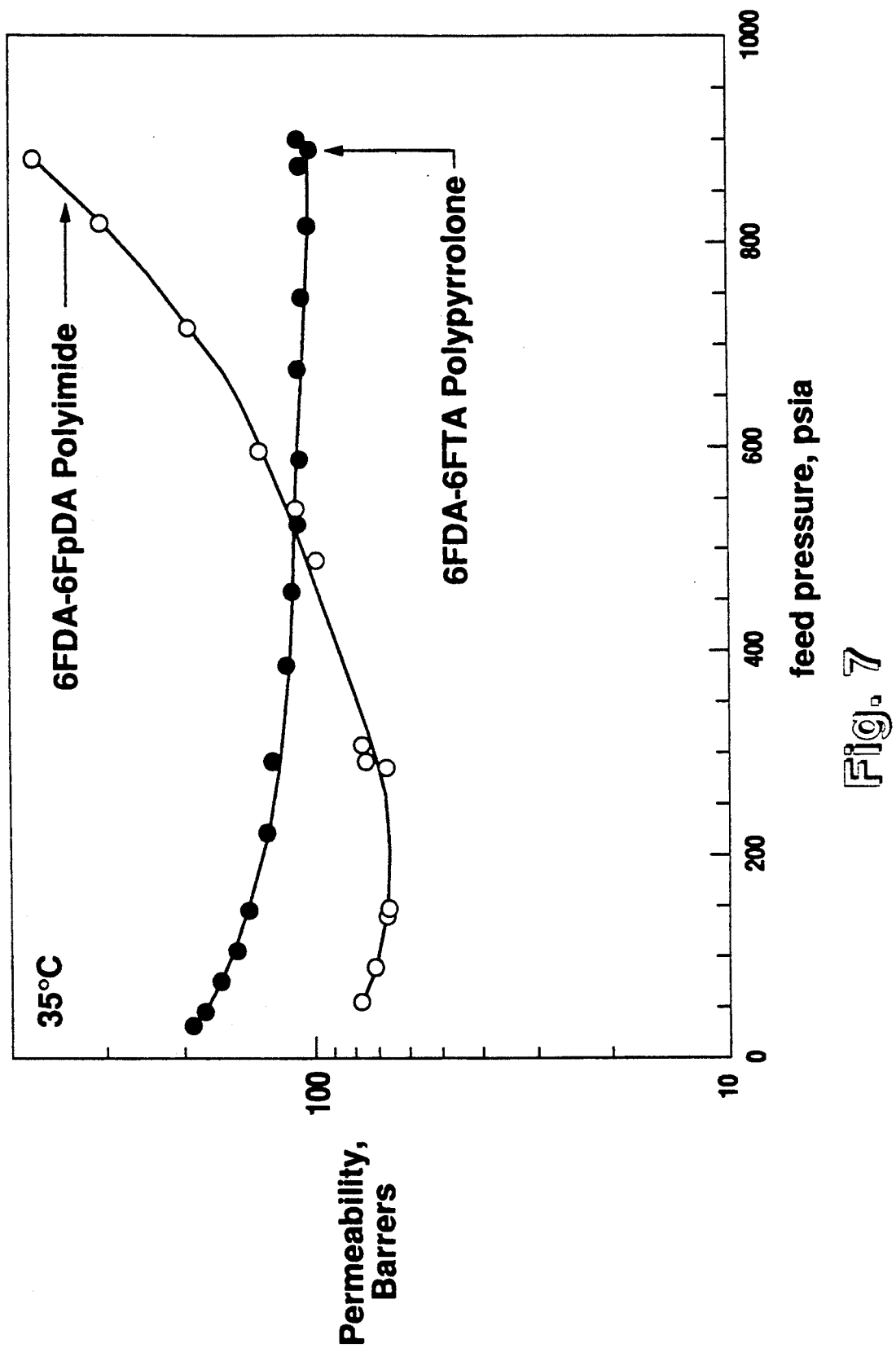
FIG. 7 demonstrates $CO_2$ permeabilities and plasticization effects on the 6FDA-6FpDA polyamide and the 6FDA-6FTA polypyrrolone.

Further indication of the superior plasticization resistance of the polypyrrolones over the polyimides is shown in the two figures of pure gas $CO_2$ permeability as a function of pressure (FIGS. 6 and 7). The three polypyrrolones taken to high feed pressures show only modest increases in permeability and only after pressures of above 600–700 psia. In fact the permeabilities of the polypyrrolones do not increase above the initial values. The 6FDA-6FTA polypyrrolone and the 6FDA-6FpDA are compared in FIG. 7. Clearly the $CO_2$ permeability of the 6FDA-6FpDA increases many times over the pressure range of 50 psia (about 70 Barrers) to 900 psia (about 400 Barrers). The increase in $CO_2$ permeability begins at a pressure of about 200 psia for the 6FDA-6FpDA polyimide which is considerably lower than the 600–700 psia for the polypyrrolones. The large permeability increase is due to a large diffusivity increase which indicates the polyimide is being softened by the $CO_2$. Such softening leads to plasticization which is manifested as the loss of selectivity in a mixed gas application.

EXAMPLE 6

Procedure for Permeability Measurement of Dense Films

Figure 11:
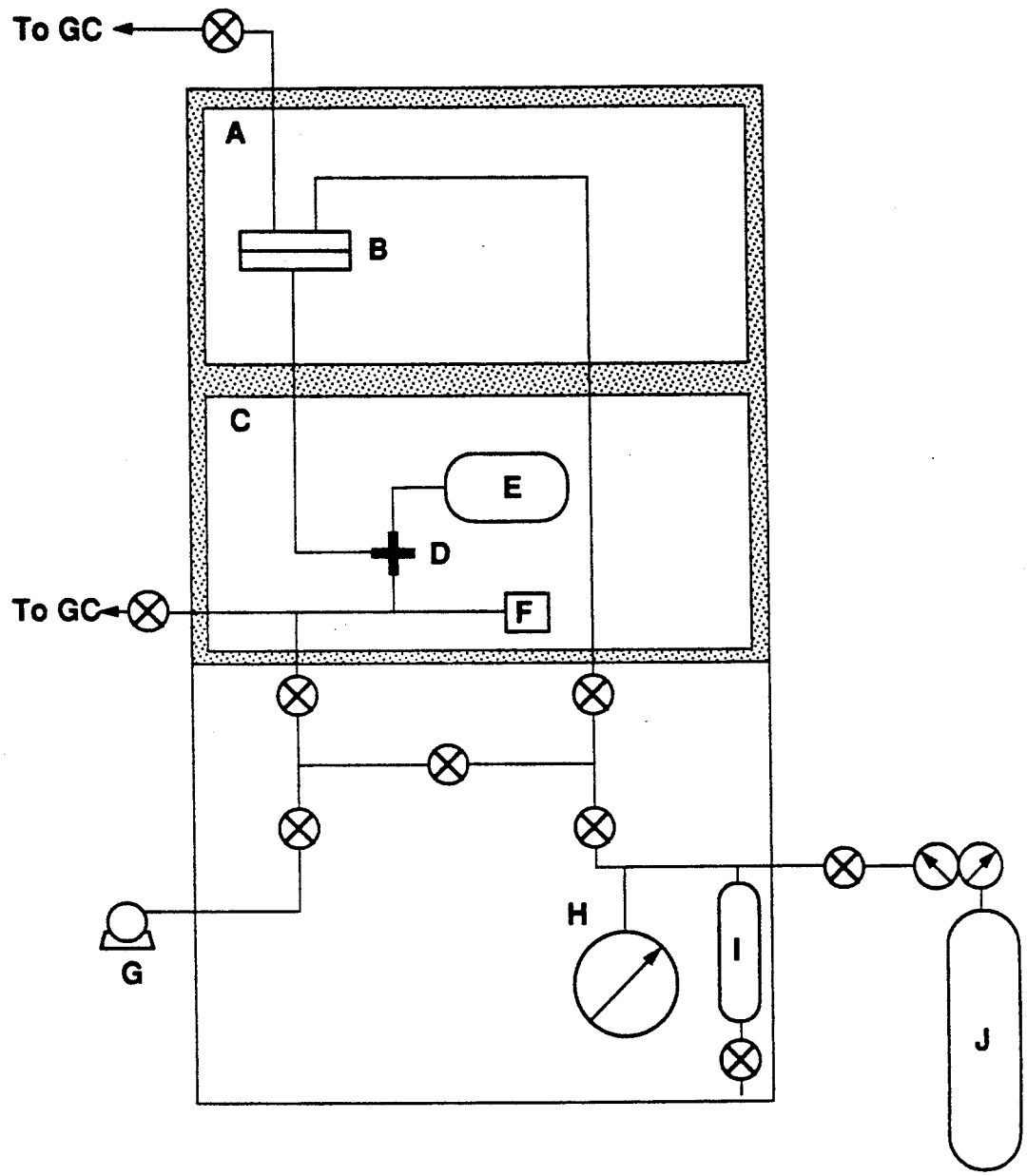
FIG. 11 is a diagram of a permeation apparatus discussed in Example 6.

Dense film permeabilities were measured using the manometric, or constant volume, method and is shown in FIG. 11. Our equipment includes a MKS Baratron® transducer with a range of 0–10 torr for monitoring the accumulation of gas in the downstream, a 0–1000 psia, Heisee gauge for measuring the upstream pressure, stainless steel tubing for plumbing, Nupro® bellows seal valves, and Cajon VCR® metal face seal connections. The receiver volume and permeation cells are kept in separate thermostated chambers. The permeation cell temperature can be varied from 25° C. to 65° C. with 35° C. being the usual temperature. The downstream receiver volume was kept at 35° C. to allow the pressure transient recorded with a strip chart to be converted to a flux.

The dense films were masked between two rings of aluminum foil tape to give a defined area available for permeation. Typical areas used are 9.35 $cm^2$ and 2.54 $cm^2$. These areas were well defined since the foil tape is die cut. The thickness of the films within the diameter of the ring were measured between ten and twenty times to determine an average thickness and standard deviation, ensuring the film is relatively uniform in thickness. Typical thicknesses are between 4–6 mils or thousands of an inch. The film/foil assembly was then mounted within the permeation cell either one of two ways. Larger films could be installed in a double O-ring seal cell, but smaller films used the epoxy sealing method. The two methods differ in how the upstream feed gas is contained. The epoxy method also has the limitation of not exposing the epoxy to high levels of highly sorbing penetrants, such as carbon dioxide at 500 psia. Such exposure could soften the epoxy and compromise the seal, allowing a catastrophic leak of the upstream into the downstream of the permeation apparatus. The epoxy used is a 5-minute brand and is allowed to dry to 24-hours at 35° C. Although larger films were needed to ensure a seal with the double O-ring method, the concern of highly sorbing penetrants is avoided.

The cell and film were attached to the system and both the upstream and downstream faces of the film were evacuated for two days to remove sorbed gases and moisture. The upstream and downstream were then separated and the upstream pressurized with initially 2 atm. of gas while the downstream was closed off from the vacuum pump. The chart recorder was started immediately to make a time lag measurement. This records the response of the film to the first exposure of gas, and helps determine when the flux of the gas has reached steady state. The upstream pressure was maintained for ten time lags to ensure steady state is reached and another flux measurement is made. The permeabilities were calculated as follows:

$$\text{Permeability, } P [=] \text{Barrers, 1 Barrer} = 10^{-10} \frac{cc(STP)}{cm\ sec\ cm\ Hg}$$

$$\frac{dp}{dt} [=] \frac{torr}{min}$$

V=downstream volume [=]cc
l=film thickness [=]mils
T=reservoir temperature [=]K
A=film area [=]$cm^2$
$\Delta p$=pressure drop across film [=] psia $$P = \frac{\left(\frac{dp}{dt}\right) \cdot (2.94 \times 10^4) \cdot (V) \cdot (l)}{(T) \cdot (A) \cdot (\Delta p)}$$

After each steady state measurement, the upstream pressure was increased and the downstream evacuated, at least ten time lag periods were waited, and another steady state measurement made. When switching from one gas to another, the upstream feed pressure was slowly bled off and both the upstream and downstream face of the film were evacuated as prior to the time lag measurement. Time lag measurements were not made for helium which equilibrated within seconds after pressurization of the film.

Ideal selectivities are simply the ratios of pure gas permeabilities. With the measurement of solubilities, diffusivities and the component selectivities can be determined.

P=D S $$S[=] \frac{cc(STP)}{cc\ atm}$$

$$D [=] \frac{cm^2}{sec} = \frac{l^2 6P}{S}$$

$$\alpha A/B = \frac{P_A}{P_B} = \frac{D_A S_A}{D_B S_B}$$

Actual $CO_2/CH_4$ selectivities and mixed gas permeabilities were measured using a mixed gas feed for the upstream. The feed was passed across the film so that the stage cut (stage cut is defined as the ratio of the amount of gas permeated through membrane to the amount of gas fed to the membrane) is less than 1%, thus a constant concentration is maintained on the upstream of the membrane without boundary layer effects. The upstream feed was analyzed 4 times with a GC and an average value of the composition was used. A permeation measurement was made after ten time lags for the slower of the two gases, methane, had passed. The downstream pressure was allowed to build to 10 Torr and 4 samples of the downstream composition were taken. The permeability of the mixture is calculated as above, but this is for the mixture. The permeability of each component was calculated separately after completing the downstream compositional analyses.

$X_a$, $X_b$=upstream mole fractions of the two components a and b
$Y_a$, $Y_b$=downstream mole fractions of the two components a and b $$P_a = \frac{PY_a}{X_a}$$

$$P_b = \frac{PY_b}{X_b}$$

Thus $a_{a/b} = \frac{P_a}{P_b} = \frac{X_b Y_a}{X_a Y_b}$

The procedure between subsequent permeation measurements after increasing the pressure of the upstream feed was similar to the pure gas measurement procedure.

Figure 12:
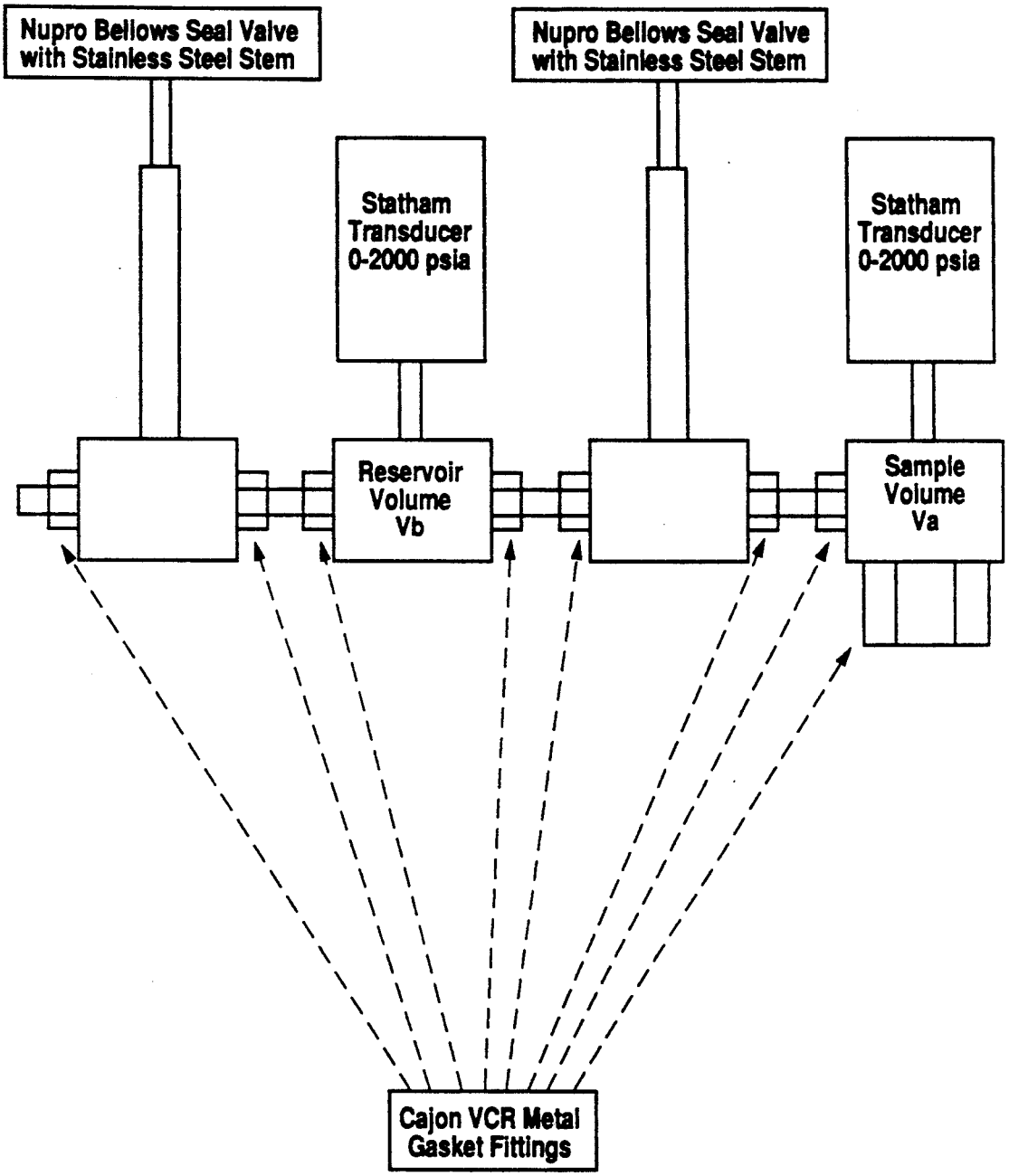
FIG. 12 is a diagram of a sorption apparatus, a pressure decay cell used for measuring sorption levels in a polymer.

The sorption cell shown in FIG. 12 utilized the pressure decay method for the measurement of the sorption levels of the gases in the polymers. The pressure decay method relies on accurate pressure measurements in two known volumes to determine the molar quantity in the gas phase at any moment. Sorption levels were determined by calculating the difference between the amount of gas in the gas phase before and after an expansion of gas from the reservoir chamber to the sample chamber. The pressure decay method is not suitable for use with vapors under conditions which would allow condensation since liquid phase quantities would be indeterminable. For such conditions a gravimetric determination of sorption levels would be necessary using a quartz spring or electrobalance to measure mass uptake by the polymer sample.

EXAMPLE 7

Poly(imide-co-pyrrolones)

The polypyrrolones may be somewhat brittle in their final form. Their films may undergo little strain before tensile failure because they are rigid materials. The toughness of the films could likely be increased by copolymerization of diamine with the tetramine to form poly(imide-co-pyrrolones). An example would be a copolymer of 6FDA with ODA and TADPO. The expected transport properties would lie between the properties of the homopolymers 6FDA-ODA and 6FDA-TADPO. The permeabilities and selectivities of the copolymer may be greater than the polyimide, except for the ideal permselectivity of the carbon dioxide/methane pair. The mixed gas selectivity of the copolymer may be expected to be greater than the polyimide since the polypyrrolone segments offer greater resistance to plasticization than the polyimide segments. The polyimide content should be minimized to avoid early onset of plasticization.

The polypyrrolones are not sufficiently soluble in the final form, so films of their polyamide precursors were cast and thermally cured at 285° C. to the polypyrrolones for testing in our labs. The polyamides are soluble in polar aprotic solvents such as N,N-dimethylacetamide (DMAc). The polypyrrolone results thus far have been obtained on dense films about 4 mils or $10^6$ Å thick. A useful membrane thickness is of the order of 1000 Å achieved by the formation of either integrally-skinned asymmetric membranes or thin film composite membranes. The technique of forming an integrally-skinned membrane requires concentrated solutions, sometimes containing a volatile solvent. Obtaining useful membranes may prove difficult due to the thermal cure. Copolymerization might give materials which are soluble in their final form, making the formation of membranes feasible. However, the entire structure is composed of the same material, thus materials cost is a concern. Copolymerization of an expensive tetramine, whose transport properties are desirable, with a less expensive diamine may be an economically attractive alternative.

Thin film composites require a dilute solution of the polymer in a solvent that would not alter the porosity of the supporting polymer layer. Such solvents offer challenges in the formation of composites in that they must be non-solvents and perhaps even non-swellers of the support layer. With the polypyrrolones the support layer would have to possess the thermal stability to undergo the curing process. Copolymerization so that the polymers are soluble in "weaker" solvents and/or in their final form would be advantageous. The polyimides based on 6FDA and diamines are soluble in halogenated hydrocarbons, thus copolymerization offers some possibility of improving the solution characteristics desired.

The following literature references are incorporated in pertinent part by reference herein for the reasons cited in the text.

REFERENCES

Bailar, J. C. et al., Quarterly Reports to WADC Contract No. AF 33(616)-3209 Aug. 1958 and 33(616)-5486, May 1959).

Bell, V. L. and R. A. Jewell, Synthesis and Properties of Polyimidazopyrrolones, *Journal of Polymer Science: Part A*-1, vol. 5:3013-3060, (1967).

Bell, V. L. and G. F. Pezdirtz, Polyimidazopyrrolones: A New Route To Ladder Polymers, Polymer Letters, vol. 3, pp. 977-984, (1965)

Bell, V. L. Process for Interfacial Polymerization of Pyromellitic Dianhydride and 1,2,4,5-Tetraamino-Benzene, U.S. No. 3,518,232, dated Jun. 30, 1970.

Berlin et al., Thermostable Polymers from Dianhydrides of Aromatic Tetracarboxylic Acids and Tetraamine, *Russian Chemical Reviews*, 40: (3), 1971.

Berry G. C. and P. R. Eisaman, Cryoscopy on Sulfuric Acid Solutions of a Heterocyclic Polymer (BBB) and Related Compounds, *Journal of Polymer Science*,- 12:2253-2266 (1974).

Bondi, A. A., Physical Properties of Molecular Crystals, Liquid and Glasses, Wiley, New York, N.Y., 1968, chap. 14.

Bruma, M. and C. S. Marvel, Synthesis of a Pyrrolone-Type Polymer Containing Anthraquinone Units in Molten Antimony Trichloride, Journal of Polymer Science, vol. 12, 2385-2389 (1974).

Coleman's, M. R., Ph.D. dissertation "Isomers of Fluorine Containing Polyimides for Gas Separation Membranes", 1992.

Colson et al., Polybenzoylenebenzimidazoles, *Journal of Polymer Science*, vol. 4, 59-70 (1966).

Cryer, J. U.S. Pat. No. 2,894,988 dated Jul. 14, 1959

Dawans, F. and C. S. Marvel, Polymers from ortho Aromatic iq Tetraamines and Aromatic Dianhydrides, *Journal of Polymer Science*, vol. 3, pp. 3549-3571 (1965).

European Patent Application, 0446947A2, dated Sept. 18, 1991.

Foster, R. T., and Marvel, C. S., "Polybenzimidazoles. IV. Polybenzimidazoles Containing Aryl Ether Linkages", *J. Polym. Sci.:* Part A, 3 (1965) 417.

Hayes R. A., U.S. Pat. No. 4,717,394 dated Jan. 5, 1988

Hayes R. A., U.S. Pat. No. 4,705,540 dated Nov. 10, 1987

Ho et al., Polyimide/Aliphatic Polyester Copolymers, U.S. Pat. No. 4,944,880, dated Jul. 31, 1990.

Ho et al., Polyimide Aliphatic Polyester Copolymers, U.S. Pat. No. 4,990,275, dated Feb. 5, 1991.

Hughes, et al., Method for Forming Pyrrone Molding Powders and Products of Said Method, U.S. Pat. No. 3,657,190, dated Apr. 18, 1972.

Kim, T. H. et al., "Relationship Between Gas Separation Properties and Chemical Structures in a Series of Aromatic Polyimides", *J. Memb. Sci.*, 37 (1988a) 45.

Kim, T. H. et al., "Advanced Gas Separation Membrane Materials: Rigid Aromatic Polyimides", J. Separation Science and Technology, 23 (1988b) 1611.

Kim's T. H., Ph.D. dissertation "Gas Sorption and Permeation in a Series of Aromatic Polyimides", 1988c.

Kohn et al., Method of Gas Separation and Membranes Therefor, U.S. Pat. No. 5,074,891 dated Dec. 24, 1991.

Koros, W. J. and D. R. B. Walker, Gas Separation Membrane Material Selection Criteria: Weakly and Strongly Interacting Feed Component Situations, *Polymer Journal*, vol. 23, no. 5, pp.481–490 (1991).

Saferstein L., Polymerization of Benzimidazobenzophenanthroline-Ladder Polymer, U.S. Pat. No. 3,792,024, dated Feb. 12, 1974.

Scott et al., Polyimidazopyrrolone Reverse Osmosis Membranes, *Polymer Letters*, vol. 8, pp.563–571 (1970).

Thaler et al., Crosslinked Copolymers of Aliphatic Polyester Diols and Dianhydrides, U.S. Pat. No. 4,946,594, dated Aug. 7, 1990.

Thaler et al., Crosslinked Copolymers of Aliphatic Polyester Diols and Dianhydrides, U.S. Pat. No. 4,997,906 dated Mar. 5, 1991.

Van Krevelen, D. W., and Hoftyzer, P. J., Properties of Polymers, Their Estimation and Correlation with Chemical Structure, 2nd edn., Elsevier, New York, N.Y., 1976, chap. 4.

Walker, D. R. B. and William J. Koros, Transport characterization of a polypyrrolone for gas separations, *Journal of Membrane Science*, 55:99–117 (1991).

What is claimed is:

1. A fluid separation membrane comprising a polymer having recurring units of the chemical formula

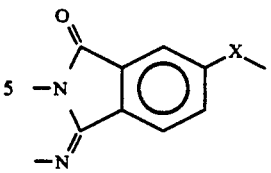

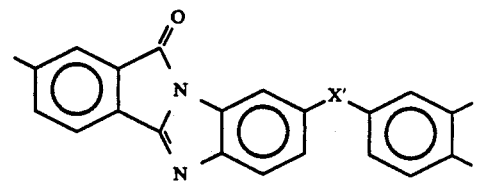

where X and X' are independently

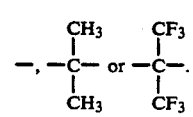

2. A method of separating two or more fluids comprising the step of bringing a mixture of two or more fluids into contact with one side of a permselective membrane which is formed from an aromatic polypyrrolone having recurring units of the formula

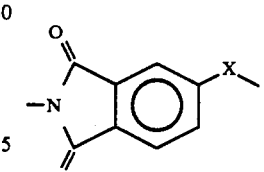

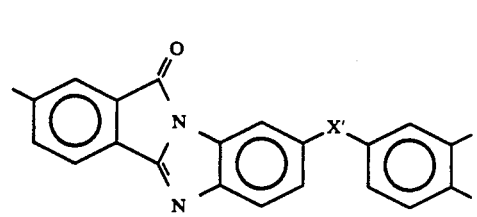

where X and X' are independently

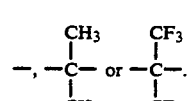

wherein one of the fluids being separated transverse the membrane at a different rate than at least one other fluid.

* * * * *